United States Patent
Boyles et al.

(10) Patent No.: US 7,125,951 B2
(45) Date of Patent: Oct. 24, 2006

(54) MONOMERS CONTAINING AT LEAST ONE BIARYL UNIT AND POLYMERS AND DERIVATIVES PREPARED THEREFROM

(75) Inventors: David A. Boyles, Rapid City, SD (US); John T. Bendler, Annapolis, MD (US)

(73) Assignee: South Dakota School of Mines and Technology, Rapid City, SD (US)

( * ) Notice: Subject to any disclaimer, the term of this patent is extended or adjusted under 35 U.S.C. 154(b) by 0 days.

(21) Appl. No.: 10/692,970

(22) Filed: Oct. 24, 2003

(65) Prior Publication Data
US 2004/0254327 A1 Dec. 16, 2004

Related U.S. Application Data

(60) Provisional application No. 60/456,615, filed on Mar. 21, 2003, provisional application No. 60/421,299, filed on Oct. 24, 2002.

(51) Int. Cl.
*C08G 63/00* (2006.01)
(52) U.S. Cl. ............... 528/196; 528/198; 568/717; 568/718
(58) Field of Classification Search ........... 568/717, 568/718; 528/196, 198
See application file for complete search history.

(56) References Cited

U.S. PATENT DOCUMENTS

| | | | |
|---|---|---|---|
| 3,065,205 A | 11/1962 | Bonner | |
| 4,008,203 A | 2/1977 | Jones | |
| 4,108,837 A | 8/1978 | Johnson et al. | |
| 4,460,798 A * | 7/1984 | Klopfer et al. | 568/723 |
| 4,806,601 A * | 2/1989 | Percec | 525/391 |
| 4,841,009 A * | 6/1989 | Kelsey | 528/75 |
| 5,281,689 A | 1/1994 | Bendler et al. | |
| 5,290,656 A * | 3/1994 | Uetani et al. | 430/165 |
| 5,319,149 A * | 6/1994 | Bendler et al. | 568/718 |
| 6,055,096 A * | 4/2000 | Michihata et al. | 359/352 |

FOREIGN PATENT DOCUMENTS

| | | |
|---|---|---|
| GB | 621102 | 4/1949 |
| GB | 636429 | 4/1950 |
| GB | 971227 | 9/1964 |
| GB | 1016245 | 1/1966 |
| GB | 1060546 | 3/1967 |
| GB | 1078234 | 8/1967 |
| JP | 2003-146924 * | 5/2003 |

OTHER PUBLICATIONS

Coleen Pugh and Virgil Percec: Synthesis of thermotropic side chain liquid crystal polymers, Macromolecular Chemistry and Physics, vol. 201, Issue 12, pp. 1303-1310, Aug. 10, 2000.*
Virgil Percec et al."Molecular design on novel liquid crystalline polymers with complex archiecure: Macrocyclics and dendrimers" Pure & Apl. Chem. vol. 67, No. 12, pp. 2031-2038, 1995.*
Christoph Wutz *and Dana Schleyer: "Conformation of spacers in smectic poly(ester imide)s" Institut für Technische und Makromolekulare Chemie, Universität Hamburg, Bundesstrasse 45, D-20146 Hamburg, Germany Received: Jun. 23, 1997; Accepted: Mar. 3, 1998.*
LeGrand, Donald G. and John T. Bendler, "Handbook of Polycarbonate Science and Technology", Chap. 5 "Nonbisphenol A Polycarbonates", New York: Marcel Dekker, Inc., 2000; ISBN 0824799151.
H.A. Vogel, Polyarylsulfones. "Synthesis & Properties", Journal of Polymer Science, Part A-1, vol. 8, 2035-2047 (1970).

* cited by examiner

*Primary Examiner*—Terressa Boykin
(74) *Attorney, Agent, or Firm*—Gordon & Rees LLP

(57) ABSTRACT

The invention relates to bisphenol monomers containing one or more biaryl units and related polymers, derivatives and resins thereof and more particularly to Bisphenol monomers containing two biaryl units separated by a spacer group X, and to bisphenol monomers containing a biaryl unit and an aryl unit separated by a spacer group X, and to polymers, derivatives, resins and related products prepared therefrom.

29 Claims, 9 Drawing Sheets

Various Tetraaryl Analogues

Bisaniline P and Bisaniline M Tetraaryls

Formal Tetraaryl Analogues 1,1-dichloro-2,2-bis[4-(2'-hydroxyphenyl)phenyl]ethene 2,2-bis[4-(2'-hydroxyphenyl)phenyl]propane 1,1-dichloro-2,2-bis[4-(3'-hydroxyphenyl)phenyl]ethene 2,2-bis[4-(3'-hydroxyphenyl)phenyl]propane 1,1-dichloro-2,2-bis[4-(4'-hydroxyphenyl)phenyl]ethene 2,2-bis[4-(4'-hydroxyphenyl)phenyl]propane

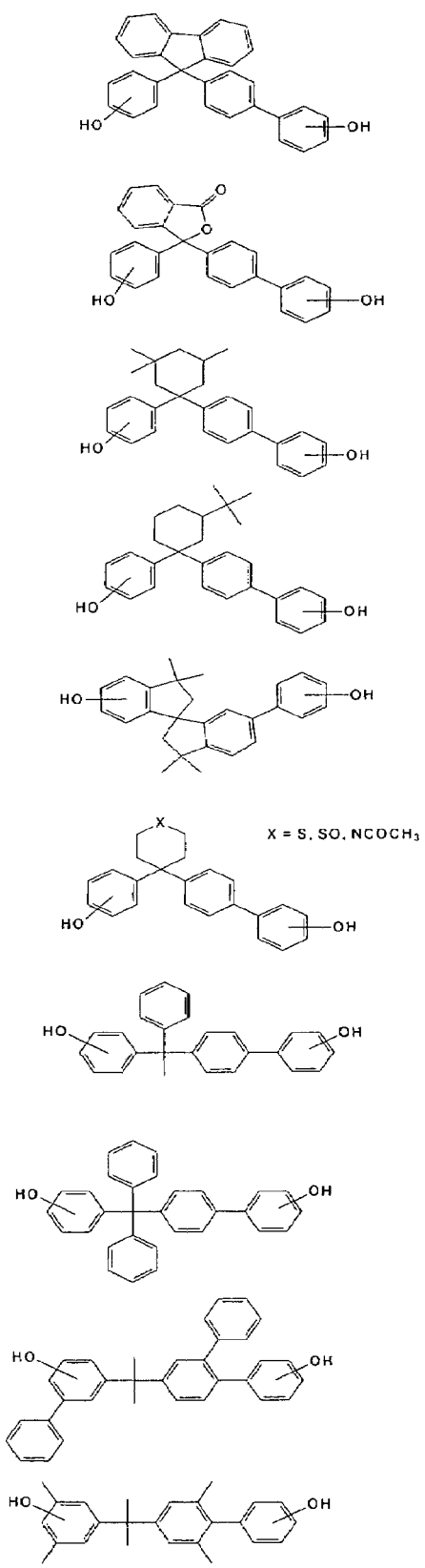
Figure 3A. Asymmetric Bisphenols of the Present Invention.

X = S, SO, NCOCH₃

MONOMERS CONTAINING AT LEAST ONE BIARYL UNIT AND POLYMERS AND DERIVATIVES PREPARED THEREFROM

CROSS-REFERENCE TO RELATED APPLICATION

Priority is claimed from U.S. Provisional Patent Application No. 60/421,299 filed on Oct. 24, 2002 and from U.S. Provisional Patent Application No. 60/456,615 filed on Mar. 21, 2003. The entire disclosures of those provisional applications are considered to be part of the disclosure herein and are incorporated by reference.

FIELD OF THE INVENTION

The invention relates to bisphenol monomers containing one or more biaryl units and related polymers, derivatives and resins thereof and more particularly to Bisphenol monomers containing two biaryl units separated by a spacer group X, and to bisphenol monomers containing a biaryl unit and an aryl unit separated by a spacer group X, and to polymers, derivatives, resins and related products prepared therefrom.

BACKGROUND OF THE INVENTION

Bisphenols are commonly used as monomers in the preparation of a wide variety of polymers, including polyethersulphones, polyetherketones, polyarylates, polyetherimides, polyphenylene oxides, epoxy resins and cyanate resins, cyanate ester resins and polycarbonates. Polycarbonates are a group of polymers that exhibit relatively high transparency, high ductility, high impact strength and low weight. These characteristics make polycarbonates suitable for a wide variety of products and uses, and particularly suitable for shatterproof windows, lightweight eyeglass lenses, other lenses such as vehicle headlamps and the like. The principal commercial polycarbonate is known as LEXAN (R) and is available from The General Electric Company of Stamford, Conn. This particular polycarbonate is also known as the polycarbonate of Bisphenol A because it is made from Bisphenol A and phosgene. Bisphenol A may be depicted by the following formula.

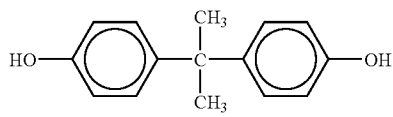

Notwithstanding the advantageous properties of polycarbonates made from Bisphenol A, it has been attempted to improve one or more of its properties, such as transparency, ductility, glass transition temperature and low weight. One prior monomer essentially added an additional aryl group to each side of the Bisphenol A monomer to reportedly increase the glass transition temperature while retaining the ductility of Bisphenol A polycarbonates. See U.S. Pat. Nos. 5,281,689 and 5,319,149 ("the '689 and '149 patents"). More specifically, the '689 and '149 patents disclose bis[4-(4'-hydroxyphenyl)-phenyl] alkanes of the formula:

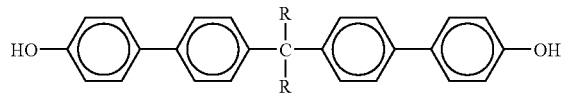

where each R is independently a $C_{1-4}$ primary alkyl or $C_{6-10}$ cycloalkyl radical, with methyl radicals preferred. These monomers were limited to the specific spacer group disclosed, i.e., each R being a $C_{1-4}$ primary alkyl or a $C_{6-10}$ cycloalkyl radical, and to the symmetrical structure of two aryl units on each side of the specified spacer group. The limitations of the spacer group to the specific groups in turn limit the types of syntheses and applications of this monomer.

Another monomer reportedly used an oxygen atom as the spacer group between the two symmetrical biaryl units. A representative formula for this structure is as follows.

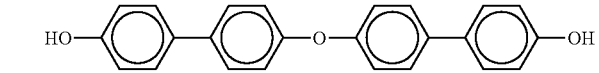

In summary, the prior bisphenol monomers generally were limited to 1) two symmetrical biaryl units separated by a limited number of specified spacer groups, namely a $C_{1-4}$ primary alkyl, $C_{6-10}$ cycloalkyl radical or an oxygen atom, and 2) two symmetrical aryl units separated by a spacer group. As such, the choice of monomers was limited, which limited the choice of starting materials and process to synthesize the desired monomers. The limited choice of monomers also limited the number and variety of polymers, derivatives, resins and other products that could be synthesized. Therefore, a need exists for improved bisphenol monomers and improved polymers made from bisphenol monomers.

DETAILED DESCRIPTION OF THE INVENTION

Figure 1A:
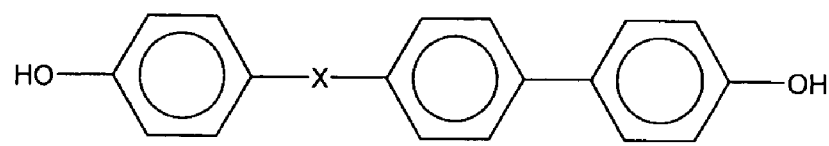
FIGS. 1A–1C depict monomers of the present invention.

The invention relates to bisphenol monomers containing one or more biaryl units and related polymers, derivatives and resins thereof and more particularly to Bisphenol monomers containing two biaryl units separated by a spacer group X, and to bisphenol monomers containing a biaryl unit and an aryl unit separated by a spacer group X, and to polymers, derivatives, resins and related products prepared therefrom.

In general, one of the embodiments of the invention disclosed herein comprises the addition of a single aryl unit to the chemical structure of any bisphenol between one of the terminal hydroxyl end groups and the rest of the bisphenol, or between one aryl unit and the spacer group X. Another embodiment of the invention disclosed herein comprises the addition of an aryl unit to the chemical structure of any bisphenol between each of the two terminal hydroxyl end groups and the rest of the bisphenol, or between each of the two aryl units and the spacer group X.

The physical properties of Bisphenol A, such as higher glass transition temperatures, may be enhanced by synthesizing Bisphenols with a larger mass. However, bulky side groups can decrease mechanical toughness of the resulting polymer. The desired higher glass transition temperature may be achieved by designing bisphenols with masses larger than bisphenol A, while improving toughness by keeping monomer center-of-mass distances small and aspect ratios large.

As used herein, the term aryl unit refers to an aromatic hydrocarbon, which may be substituted or unsubstituted, having at least one hydrogen atom removed. A biaryl unit is defined as two coupled aryl units, which may be substituted or unsubstituted. The following is a representative formula of a biaryl unit.

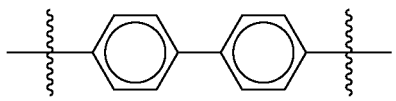

A phenol refers to a compound having a phenyl ring, which bears at least one hydroxyl group. A bisphenol refers to a compound having at least two phenyl rings, each of which bears at least one hydroxyl group. The following is a representative formula of a bisphenol, with the hydroxyl end groups shown at the para position of the terminal aryl units.

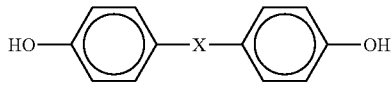

and A spacer group refers to a bridging group or radical that separates two portions of the chemical structure, e.g., one aryl unit from another aryl unit, one biaryl unit from another biaryl unit, one biaryl unit from one aryl unit.

In one embodiment, a bisphenol monomer of the present invention has a chemical structure of an aryl unit separated from a biaryl unit by a spacer group X. That is, one aryl unit is added to the chemical structure of a typical bisphenol between one of the terminal aryl hydroxyl groups and the rest of the bisphenol, or between one aryl unit and the spacer group X. The following is a representative formula of this embodiment of the invention, which is also referred to herein as an "asymmetrical" bisphenol. The structure indicates that the hydroxyl end groups may be at the para, meta or ortho position of the terminal aryl unit, including one hydroxyl end group at one of those positions and the other hydroxyl end group at a different position.

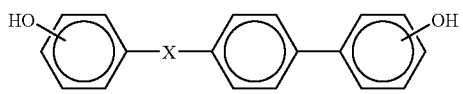

As also depicted in FIG. 1A, the following is also a representative formula of this embodiment of the invention, with both of the two hydroxyl end groups shown at the para position of the terminal aryl unit.

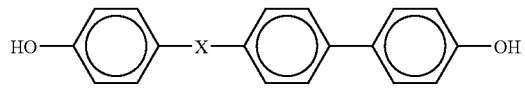

In another embodiment of the invention, a bisphenol monomer comprises two biaryl units separated by spacer group X. That is, an aryl unit is added to the chemical structure of a typical bisphenol between each of the two terminal hydroxyl groups and the rest of the bisphenol, or between each of the two aryl units and the spacer group X. Unlike the '689 and '149 patents, the spacer group X is not limited to a spacer group R—C—R, wherein R is independently a $C_{1-4}$ primary alkyl or a $C_{6-10}$ cycloalkyl. The following is a representative formula of this embodiment of the invention, which is also referred to herein as a symmetrical bisphenol. The structure indicates that the hydroxyl end groups may be at the para, meta or ortho position of the terminal aryl unit, including one hydroxyl end group at one of those positions and the other hydroxyl end group at a different position.

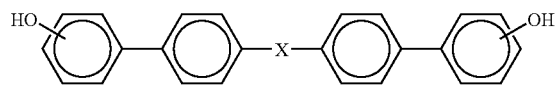

Figure 1B:
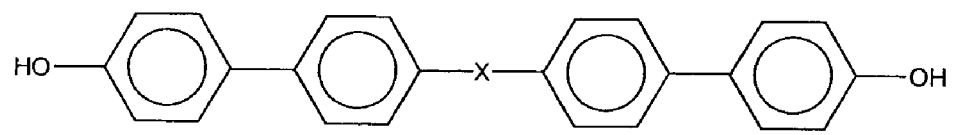

As also depicted in FIG. 1B, the following is also a representative formula of this embodiment of the invention, with both of the two hydroxyl end groups shown at the para position of the terminal aryl unit.

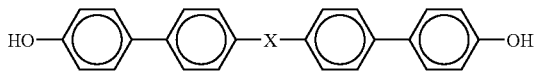

Figure 1C:
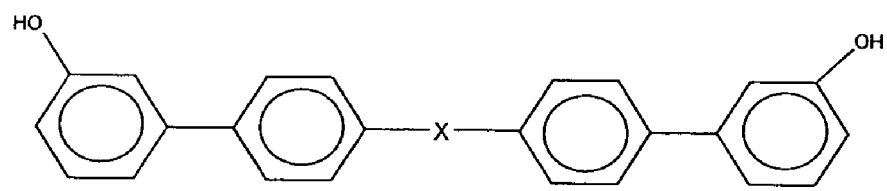

In either the asymmetric or symmetric embodiments, the biaryl unit may be unsubstituted or may be substituted, e.g., any or all of the hydrogen atoms may be substituted with halogen atoms or carbon groups. Similarly, if present, the aryl unit may be unsubstituted or may be substituted, e.g., any or all of the hydrogen atoms may be substituted by halogen atoms or carbon groups. Such substitution(s) may be used to impart different characteristics to the monomer and resulting polymer. For example, substituted halogen atoms can impart flame resistance to polymers. Also, the invention includes isomeric alternatives of both the asymmetrical and the symmetrical monomers depicted above, such as depicted in FIG. 1C. That is, the hydroxyl end group alternatively may be at the para, meta, or ortho position of the terminal aryl units, or alternatively, one hydroxyl end group may be at one of such positions, while the other hydroxyl end group is at a different position, e.g., on para and one meta.

Figure 2A:
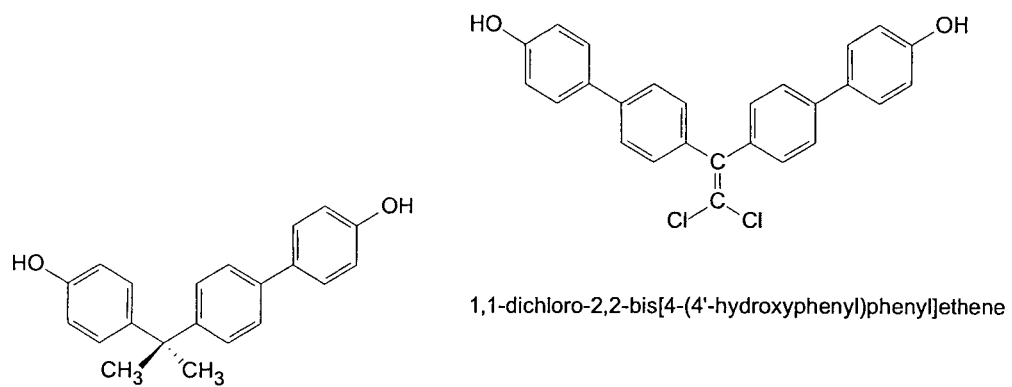
FIGS. 2A–2C depict representative monomers of the present invention that have been synthesized.
Figure 2B:
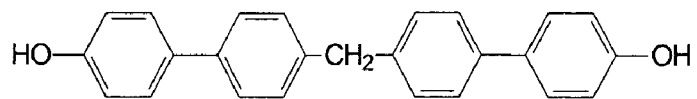
Figure 2B:
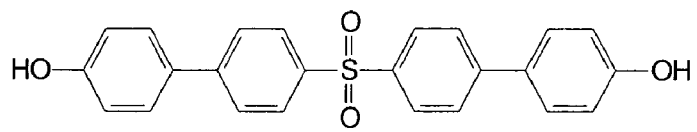
Figure 2B:
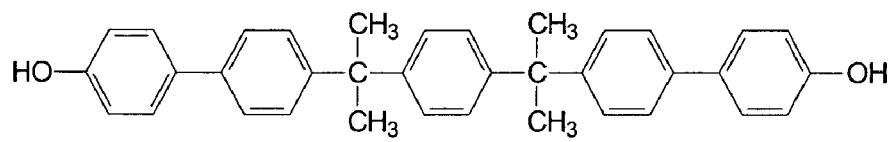
Figure 2B:
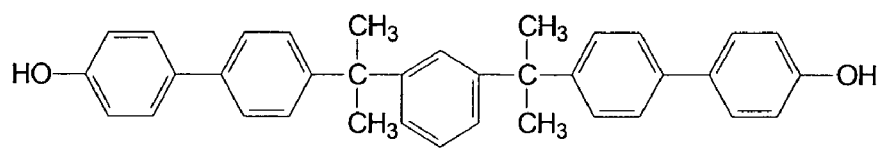
Figure 2B:
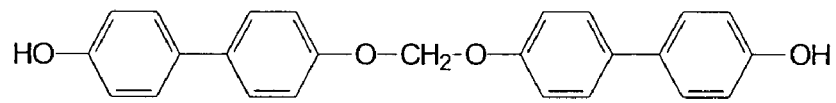
Figure 2B:
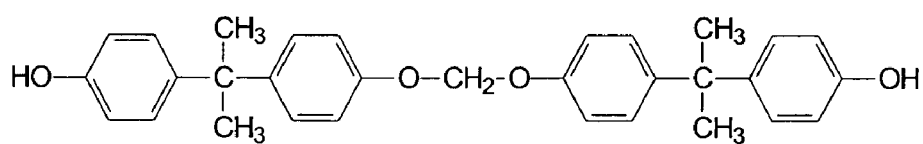
Figure 2C:
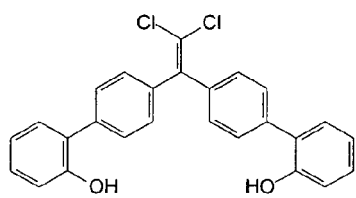
Figure 2C:
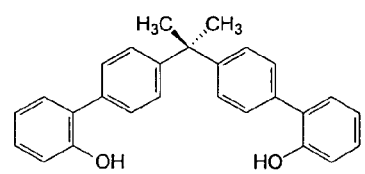
Figure 2C:
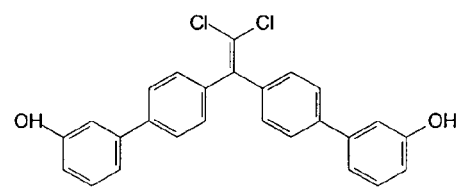
Figure 2C:
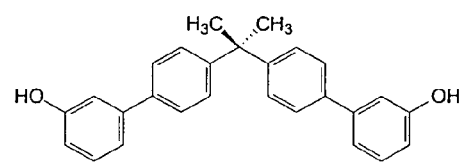
Figure 2C:
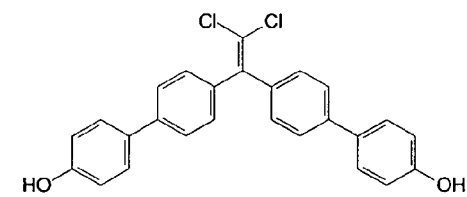
Figure 2C:
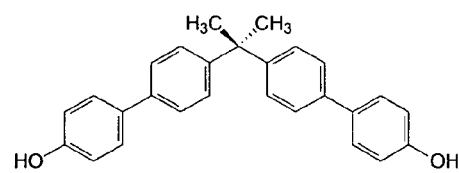
Figure 3B:
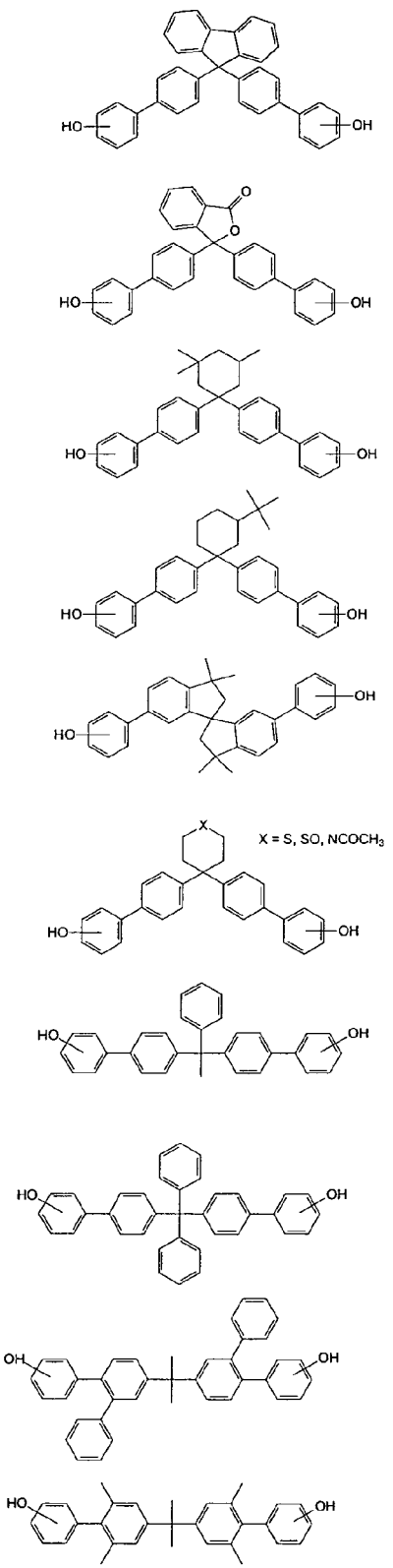
FIG. 3 depicts representative additional monomers of the present invention.

Representative bisphenols of the present invention that have been synthesized are shown in FIGS. 2A–2C, and additional bisphenols of the present invention are shown in FIG. 3.

In other embodiments of the invention, monomers of the present invention may be used in the synthesis of derivative compounds. For example, the hydroxyl end groups may be replaced with other end groups, such as dimethylacrylates, diglycidyl ethers and dicyanates, and other groups, that are suitable or desirable for the synthesis of polymers, resins and related compositions.

Figure 4:
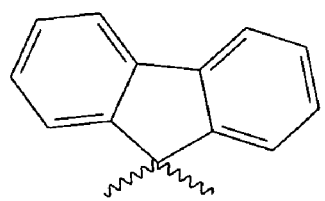
FIG. 4 depicts representative examples of spacer group X in the monomers of the present invention.
Figure 4:
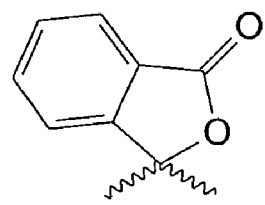
Figure 4:
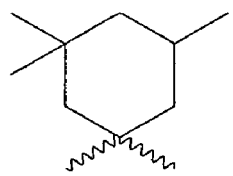
Figure 4:
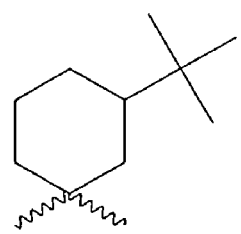
Figure 4:
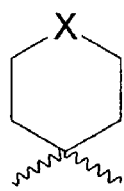
Figure 4:
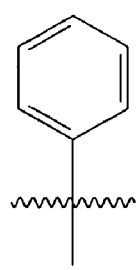
Figure 4:
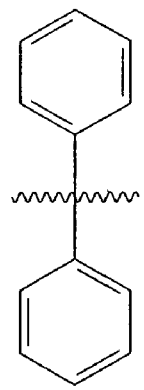
Figure 5:
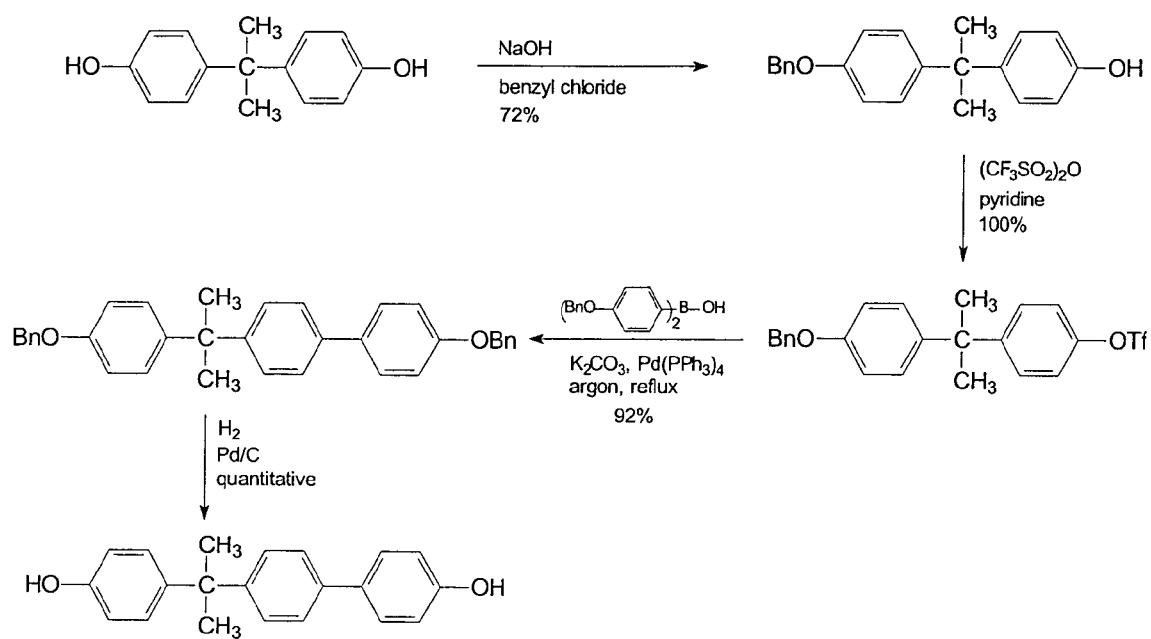
FIG. 5 is a process diagram depicting the synthesis of a monomer of the present invention.
Figure 6:
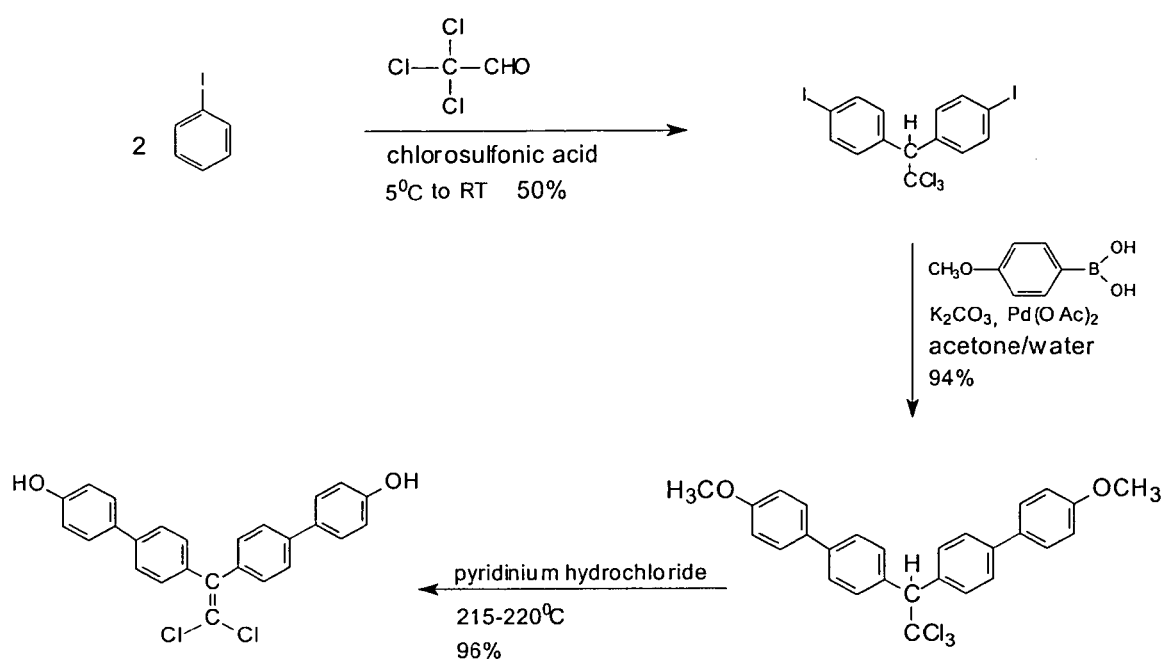
FIG. 6 is a process diagram depicting the synthesis of another monomer of the present invention.

The spacer group X may be any of a wide variety of radicals, including substituted and unsubstituted alkyl and/or aryl radicals, substituted and unsubstituted alkenes, carbonyl radicals, sulfides, sulfones, sulfoxides, and combinations thereof, among many others. Examples of spacer groups X from commonly available starting materials with relatively straightforward syntheses include $CH_2$, $O-CH_2-O$, $C=O$, $O=S=O$, $F_3C-C-CF_3$, $C=CCl_2$, $(CH_3)_2C$-aryl unit-$C(CH_3)_2$, among many others. FIG. 4 depicts examples of spacer group X for the present invention.

The bisphenol monomers of the present invention may be synthesized from a variety of starting materials. For example, other bisphenols may be used to synthesize the bisphenols of the present invention, including, but are not limited to, the examples given in LeGrand, Donald G. and Bendler, John T., "Handbook of Polycarbonate Science and Technology Plastics Engineering, 56," Marcel Dekker, 2000, ISBN 0824799151. In addition to other bisphenols, compounds that are not bisphenols, such as bisarylhalides, also may be used to synthesize the bisphenol monomers of the present invention, as would be recognized by those skilled in the art.

Bisphenols commercially known which may be converted chemically to bisphenols of the present invention include but are not limited to the following. Each of these bisphenols, as well as other available bisphenols, may be used to synthesize a bisphenol of the present invention by either 1) the addition of a single aryl unit to the chemical structure of the prior bisphenol between one of the terminal hydroxyl end groups and the rest of the prior bisphenol, or between one of the aryl units and the spacer group X, thereby synthesizing an "asymmetrical" structure or 2) the addition of an aryl unit to the chemical structure of the prior bisphenol between each of the two terminal hydroxyl end groups and the rest of the prior bisphenol, or between each of the two aryl units and the spacer group X, thereby synthesizing a "symmetrical" structure.

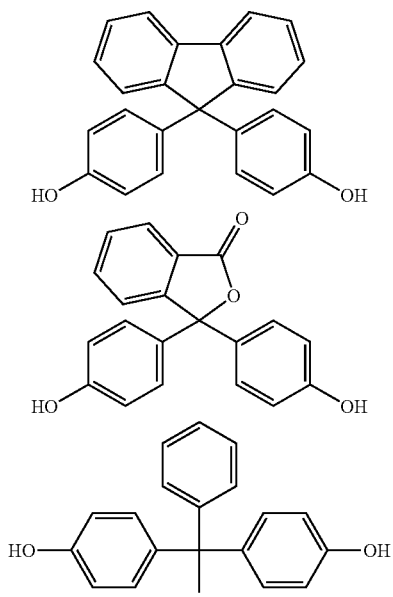

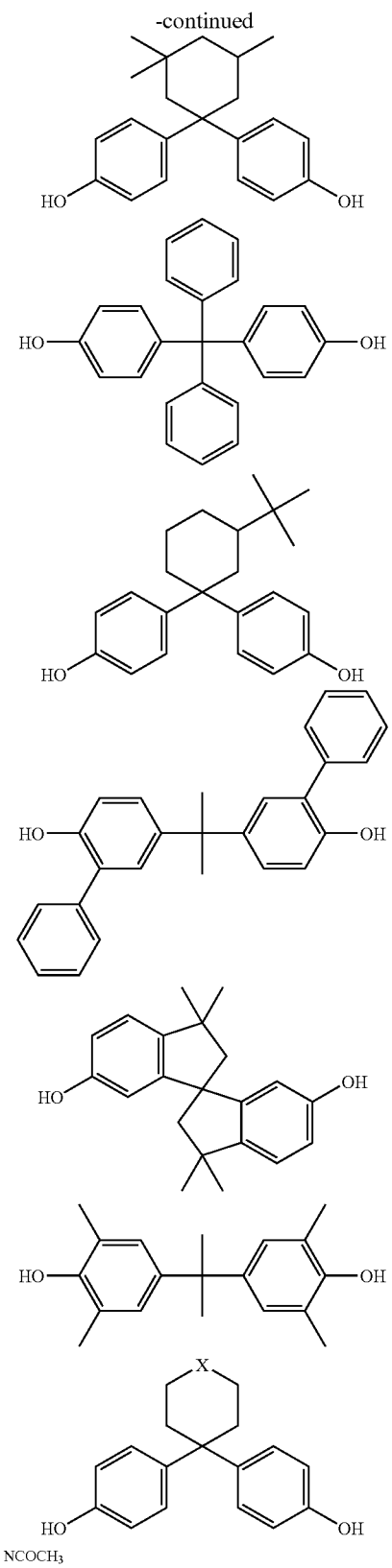

$X = S, SO^2, NCOCH_3$

Additional examples of available bisphenols that may be converted to bisphenols of the present invention may be found in the book by D. G. LeGrand and John T. Bendler, *Handbook of Polycarbonate Science and Technology*, New York: Marcel Dekker, 2000.

The bisphenol monomers of the present invention also may be synthesized through a variety of processes and combination of processes. One example of a synthesis strategy that may be used to make bisphenol monomers of the present invention utilizes an aryl coupling reaction, such as the Stille reaction or the Suzuki reaction.

Earlier aryl coupling reactions relied on the use of aryl iodides heated with activated copper powder as in the Ullmann reaction (F. Ullmann, *Ann*. 1904, 332, 38). While such reactions were of utility for relatively simple biphenols, they worked poorly for asymmetric molecules having sensitive organic functionalities. In 1981, Suzuki and Miyaura reported that the cross-coupling reactions of phenylboronic acids with aryl bromides in the present of palladium catalysts and base gave the desired products in good yield. (N. Miyaura, T. Yanagi, A. Suzuki, *Synth. Commun*. 1981, 11, 513). Various aryl halides, triflates or mesylate partners have since been used with organoboronic acids to synthesize asymmetric bisaryls in superior yield (N. Miyaura and A. Suzuki, *Chem. Rev*., 1995, 95, 2457; Suzuki, *J. Organomet. Chem*., 1999, 576, 147). The ready availability of organoboronic compounds and the mild conditions of the Suzuki synthesis have served to popularize the reaction. The reaction has also been extended to use a variety of catalyst systems and ligand, as well as new coupling partners. For example, the reaction has been extended to the use of diaryborinic acids (J. Hao and D. A. Boyles, "Synthesis and Suzuki reaction of Bis(4-benzylosypheny)borinic acid with the Ditriflate of Bisphenol A," 224th American Chemical Society National Meeting (Boston, Aug. 18–22, 2002, Division of Organic Chemistry), the teachings of which are incorporated by reference herein.

Here, a Suzuki reaction is a preferred aryl coupling reaction process, as a part of the synthesis of monomers, polymers and derivatives of the present invention. A first reaction partner and a second reaction partner are mixed in a solvent with a catalyst, with or without added ligand, and stirred under an inert gas. In some cases, the reaction may be facilitated by refluxing at the boiling point of the solvent. In a Suzuki reaction, bisphenol monomers can be prepared from aryl triflates, mesylates, tosylates, or other starting materials, which are reacted with arylboron compounds in the presence of a catalyst to effect an aryl-aryl coupling reaction. Deprotection of the compounds can result in biaryl-containing bisphenols of the present invention.

For example, the synthesis of bisphenol bis[4-(4-hydroxyphenyl)phenyl]alkane may be performed by the conversion of Bisphenol A or a Bisphenol A homologue to a reactive biseester, such as a triflate or tosylate. Alternatively, aryl halide homologues of Bisphenol A may be used. The compounds may then be reacted under catalytic conditions comprised of a palladium, nickel or other transition metal catalyst with arylboronic, diarylborinic, or triarylboranic acids or their salts. The arylboron reagents can be conveniently prepared by the reaction of borate esters with aryl Grignard reagents, the latter made from aryl halides reacted with magnesium metal.

The Suzuki reaction between the arylester or aryl halide and the arylboron reagent may be conducted in the presence of several metal catalyst systems, such as a palladium or nickel catalyst, with or without added ligand. The resulting compounds then may be subjected to appropriate chemical deprotection methods, such as demethylation with boron tribromide or debenzylation with hydrogen gas in the presence of a palladium catalyst.

Protective groups may be used during synthesis to prohibit or inhibit undesired reactions of certain functional groups, while allowing desired reactions of others. In a preferred embodiment, two such protective groups containing methyl and benzyl ethers are used. After the desired reactions occur, the compound may be "deprotected," that is, the protective group may be removed. In the preferred embodiment above, the protective group containing methyl ether may be removed by a variety of chemical reagents, such as Lewis acids, and the protective group containing benzyl ether may be removed by hydrogenolysis. Removal of the protective groups preferably results in one of the desired bisphenol monomers of the present invention. Alternatively, the bisphenol monomers of the present invention may be synthesized using other protective groups, or no protective groups.

In the synthesis of a representative bisphenol monomer having an aryl unit separated from a biaryl unit by a spacer group X (an asymmetric compound), a symmetric or asymmetric bisphenol may be monoprotected as the corresponding benzyl ether, and the unprotected hydroxyl group is then converted to the triflate. The Suzuki reaction may then be performed on the triflate end of the molecule using a benzylated arylboron reagent. The product of this reaction may be then subjected to deprotection to remove both benzylic portective groups simultaneously, affording the desired asymmetric compound.

In the synthesis of a representative bisphenol monomer having two biaryl units separated by a spacer group X (a symmetrical compound), made from symmetric bisphenol starting materials, no monoprotection is required to be used. Rather, both hydroxyl groups may be converted to triflate and the subsequent Suzuki reaction may be performed simultaneously on both ends of the molecule bearing the two triflate groups. The product of this reaction may then be subjected to deprotection to afford the desired symmetrical bisphenolic product.

The bisphenol monomers of the present invention may be used to make polymers, including homopolymers, co-polymers, block polymers, combinations and mixtures thereof, and other variations that contain at least one of the bisphenol monomer units. Additonally, the bisphenol monomers may be chemically modified or reacted with other chemical compounds to make derivatives, such as precursors to polymers, resins and related products. Such modifications may include those commonly used to convert bisphenols to cyanate and epoxy resins. For example, the symmetric or asymmetric bisphenols may be reacted with cyanogen chloride to afford cyanates, which may then be converted to triazine resins. Alternatively, the symmetric or asymmetric bisphenols may be reacted with epichlorohydrin, converting them to glycidyl ethers that may be used as epoxy resins. Similarly, they may be reacted with acrylates for conversion to esters for subsequent conversions to resins.

For example, the bisphenol monomers of the present invention can used in processes to produce polycarbonates, polyethersulphones, polyetherketones, polyaryletherketones, and polyarylates, polyetherimides, polyphenylene oxides, epoxy resins and cyanate resins, cyanate ester resins, and other polymers or monomer-containing compositions that chemically incorporate at least one unit of the bisphenol monomer. Also, liquid crystalline polymers and other condensations and addition polymers may be made from the bisphenol monomer. In summary, the bisphenol monomers of the present invention can be used in place of or in combination with current bisphenol monomers, with useful applications wherever bisphenol compounds may be utilized.

The reduction to practice of the synthesis of bisphenols of the present invention is illustrated by the following representative examples. Mono and bisarylation of aryl triflates and halides produced bisphenols of the present invention. Molecular structures have been confirmed by spectroscopic methods, including infrared and proton nuclear magnetic resonance spectroscopy. Bisphenols synthesized included various tetraaryl analogues, such as 1,1-dichloro-2,2-bis[4-(4'-hydroxyphenyl)phenyl]ethene), Bisaniline P and Bisaniline M tetraaryls, formal tetraaryl analogues, and an asymmetric Bisphenol A (2-(4-hydroxyphenyl)-2-[4-(4'-hydroxyphenyl]propane). Polymers and co-polymers were synthesized using monomers of the present invention. The majority of polymers were synthesized by solution polymerization in pyridine using triphosgene. Derivatives of monomers of the present invention were also synthesized.

The following examples represent the results of numerous tests and results of a variety of source materials, other ingredients, conditions, and other variables. It will be understood that similar results could be attained with other conditions or combination of conditions, or with other ingredients or combination of ingredients, or with changing other variables or combination of variables. A representative list of monomers of the present invention that have been synthesized are shown in FIGS. 2A–2C. The following examples are illustrative but are not limitations of the inventions disclosed herein.

EXAMPLE 1

Synthesis of 2,2-bis[4-(4-hydroxyphenyl)phenyl]-1,1,1,3,3,3-hexafluoropropane

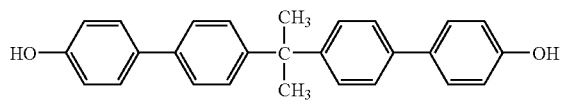

The following example sets forth a bisphenol monomer and a polymer containing a bisphenol monomer of the present invention.

The process started with the synthesis of 2,2-bis(4-trifluoromethanesulfonatephenyl)-1,1,1,3,3,3-hexafluoropropane. An oven-dried, three-necked, round-bottomed flask equipped with a magnetic stirring bar, argon gas inlet, and rubber septum was charged sequentially with 4,4'-(hexafluoroisopropylidene)diphenol (24.18 g, 71.9 mmol) and 90 ml pyridine. The solution was cooled to 0 degrees C. and trifluoromethanesulfonic anhydride (13.5 mL, 80.0 mmol) was added through the septum via syringe with stirring. The rate of addition was such that the internal temperature of the flask was kept below 25 degrees C. The solution was allowed to warm to room temperature and maintained at room temperature for 25 hours. The reaction was poured into a 250-mL separatory funnel containing 100 mL of water and 50 mL of diethyl ether. The two phases were separated, the aqueous phase extracted with four additional 50 mL portions of diethyl ether, and the combined organic layers were washed twice with 100 mL water, once with 100 mL brine, dried over anhydrous $Na_2SO_4$, and filtered. The solvent was removed on a rotary evaporator to yield a pale yellow oil which crystallized upon refrigeration. The yield was quantitative. $^1$H NMR (CDCl$_3$): δ 7.33 (4H, d, ortho to the triflate group), 7.48 (4H, d, aromatic protons ortho to isopropyl group). $^{13}$C NMR (CDCl$_3$): δ 61.91(—C(CF$_3$)$_2$), 115.74(—C(CF$_3$)$_2$), 147.45 (CF$_3$SO$_2$O—), 149.85 (aromatic carbons ortho to the triflate group), 121.05, 132.20, 133.07 (other aromatic carbons). IR (neat, cm$^{-1}$): 1509, 1436, 1328, 1289, 1254, 1206, 1139, 1019, 977, 894, 822, 783, 760, 737, 703. $M_W$=14,668; $M_N$=5,806.

2,2-bis[4-(4-benzyloxyphenyl)phenyl]-1,1,1,3,3,3-hexafluoropropane was then synthesized in the following manner. An oven-dried 500 mL one-necked round bottomed flask equipped with a stir bar was charged with a mixture of 2,2-bis(4-trifluoromethanesulfonatephenyl)-1,1,1,3,3,3-hexafluoropropane (12.01 g, 20.0 mmol), bis(4-benzyloxyphenyl)borinic acid (15.9 g, 40.3 mmol), potassium fluoride (7.67 g, 132 mmol), and 300 mL dry tetrahydrofuran. The mixture solution was purged with argon, then palladium acetate (0.90 g, 4.0 mmol) and tricyclohexylphosphine (0.14 g) was added under argon. The flask was capped with a rubber septum and stirred at room temperature for 48 hours. When the reaction had finished, the THF was removed under rotary evaporation. The residue was dissolved in 150 mL dichloromethane, filtered through a Buchner funnel with a silica gel bed, washed with 200 mL dichloromethane, and the filtrate was removed under rotary evaporation. The residue was suspended in 100 mL hexane, and the solid was filtered and air-dried to afford 9.63 g (73.3%) product. 1H-NMR: H (solvent CDCl$_3$) 5.11 (4H, s, PhCH$_2$—O—), 7.06 (4H, d, ortho to the benzyloxyl group), 7.40–7.57 (22H, m, 12H from remaining protons of biphenyl group and 10H of the benzyl aromatic protons). 13C-NMR (CDCl$_3$) 61.21 (—C(CF$_3$)$_2$), 70.06 (PhCH$_2$O—), 115.07 (—C(CF$_3$)$_2$), 115.22, 126.25, 127.47, 128.03, 128.16, 128.61, 130.57, 131.67, 132.51, 136.80, 141.19, 158.74 (aromatic carbons).

2,2-Bis[4-(4-hydroxyphenyl)phenyl]-1,1,1,3,3,3-hexafluoropropane was then synthesized in the following manner. 2,2-Bis[4-(4'-benzyloxyphenyl)phenyl]-1,1,1,3,3,3-hexafluoropropane (9.7 g, 14.8 mmol), and 10% Pd/C (0.5 g) were suspended in 400 mL of ethyl acetate and hydrogenated at normal pressure and room temperature for 96 hours. The catalyst was removed by filtration via a bed of Celite in a Buchner funnel, and the solvent was evaporated under reduced pressure and room temperature. The resulting solid was suspended in 100 mL hexane and the solid was filtered and air-dried. The yield was quantitative. 1H-NMR (CDCl$_3$) 7.44–7.56 (m, 12H), 6.92 (d, 4H, J=9 Hz).

To synthesize a polycarbonate, the bisphenol monomer 2,2-Bis[4-(4'-hydroxyphenyl)phenyl]-1,1,1,3,3,3-hexafluoropropane (0.38 g, 0.78 mmol), was dissolved in 5 mL pyridine in a 25 mL one-necked flask with stirring bar. Triphosgene (0.09 g, 0.30 mmol, 11.5% excess), was added to the pyridine solution, the flask was immediately capped with a septum and stirred at room temperature. Ten hours later the reaction mixture became yellow and was too thick for convenient stirring. The polymer was isolated by pouring the mixture into five times its volume of water with vigorous stirring. The polymer was filtered, washed with water, and suspended in 100 mL methanol at 80 degrees C. for 30 minutes with stirring. It was filtered and washed again, dried in a vacuum oven at 100 degrees C., provided 0.28 g product, 69.8%. The polymer melted at 240 degrees C. and could be cast into a film. $^1$H NMR (CDCl$_3$): δ 7.40 (4H, d), 7.50 (4H, d), 7.58 4H, d), 7.66(4H, d). IR (neat, cm$^{-1}$): 2967, 1773, 1711, 1495, 1362, 1286, 1229, 187, 1161, 1086, 1005, 821. $M_W$=40,800; $M_N$=27620.

EXAMPLE 2

Polycarbonate of Bis[4-(4'-hydroxyphenyl)phenyl]methane

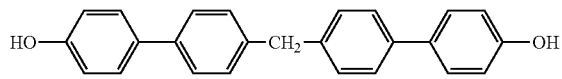

The following example sets forth another bisphenol monomer and a polymer containing a bisphenol monomer of the present invention.

The process started with the synthesis of Bis[4-iodophenyl]methane. 4,4'-Methylenebisaniline (49.57 g, 250.0 mmol), concentrated hydrochloric acid (126.0 mL) and water (126 mL) were mixed, warmed and vigorously stirred to dissolve the amine. The solution was cooled with vigorous stirring to 0–5 degrees C. by immersion in a freezing mixture of ice and rock salt. Sodium nitrite (37.26 g, 540.0 mmol), in 40 mL of water was added dropwise with stirring and the temperature of solution was maintained at 0–5 degrees C. A solution of potassium iodide (87.98 g, 530.0 mmol) in an equal weight of water was gradually added with stirring, and after the addition stirring was continued for another hour. The solution was allowed to come to room temperature, then heated gradually and cautiously in a water bath until evolution of nitrogen gas ceased. Upon cooling, a dark-colored oil settled to the bottom of the flask and solidified. The water was decanted, then 2 g sodium bisulphite was added, and the mixture was warmed, then rendered alkaline with 10% sodium hydroxide solution. The gum-like solid was extracted with three 200 mL portions of hexane. On removal of the hexane under rotary evaporation, a light yellow oil remained, which solidified to give a light yellow solid. This solid was purified by recrystallization from ethanol to give 30.3 g product (29.0%). 1H-NMR (CDCl$_3$), 3.84 (2H, s, —CH$_2$—), 6.90 (4H, d), 7.60 (4H, d). 13C-NMR (CDCl$_3$), 40.93 (—CH$_2$—), 129.97, 130.97, 137.67 (aromatic carbons).

Bis[4-(4'-methoxyphenyl)phenyl]methane was then synthesized. A 1 liter one-necked, round-bottomed flask was charged with bis(4-iodophenyl)methane (24.78 g, 59.0 mmol), 4-methoxyphenylboronic acid (16.72 g, 110.0 mol), and 500 mL acetone. Potassium carbonate (40.08 g, 290.0 mmol), in 100 mL water was added. The flask was flushed with argon gas and 0.05 g palladium acetate added. The solution immediately turned black. The flask was then flushed with argon gas and heated at reflux under positive argon pressure with vigorous stirring for five days. Reaction progress was monitored by thin layer chromatography (TLC) analysis. When the reaction finished, the heat source was removed and the reaction was allowed to cool. The acetone was removed under rotary evaporation. The residue was extracted with chloroform (3×250 mL), the organic layers were combined, filtered through a Buchner funnel fitted with a Celite filter bed. The filtrate was washed with water (3×200 mL), brine (2×200 mL) and dried over anhydrous sodium sulfate. Solvent was removed under rotary evaporation to afford a light yellow solid. The crude product was recrystallized to give an overall yield of 16.8 g, 75.0%. 1H-NMR (CDCl$_3$), 3.84 (2H, s, —CH$_2$—), 6.96 (4H, d), 7.27 (4H, d), 7.50 (8H, t). 13C-NMR (CDCl$_3$), 41.23 (—CH$_2$—), 55.40 (CH$_3$O—), 114.21, 126.89, 128.06, 129.35, 139.64, 134.01, 139.02, 158.03 (aromatic carbons).

IR (neat, cm$^{-1}$): 2920, 2873, 2234, 1890, 1607, 1582, 1529, 1498, 1548, 1432, 1401, 1292, 1253, 1210, 1183, 1222, 1037, 1000, 834, 807, 784, 717, 680, 667.

Bis-(4-(4'-hydroxyphenyl)phenyl)methane was then synthesized. A 500 mL one-necked round bottomed flask equipped with an air-cooled condenser fitted with a dropping funnel and charged with a solution of boron tribromide (18.79 g, 7.1 mL, 75.0 mmol) in 40 mL methylene chloride. A solution of bis(4-(4-methoxyphenyl)phenyl)methane (14.08 g, 37.0 mmol) in 120 mL of methylene chloride in a round-bottomed flask was cooled in an acetone-dry ice bath at −75 degrees C. The solution of boron tribromide was added dropwise to the stirred solution. When the addition was complete, the dropping funnel was replaced with a calcium chloride drying tube. The reaction mixture was allowed to attain room temperature and stand overnight with stirring. The reaction mixture was hydrolyzed by careful shaking with 200 ml of water, thus precipitating a white solid, which was washed by 5% Na OH solution and filtered out. The crude product was recrystallized from ethanol, affording 11.03 g white solid in 84.6% yield. 1H-NMR (DMSO), 6.83 (4H, d), 7.28 (4H, d), 7.47 (8H, t). 13C-NMR (CDCl$_3$), ë40.81 (—CH$_2$—), 116.14, 126.52, 128.04, 129.62, 131.26, 138.46, 139.95, 157.41 (aromatic carbons). $^1$H NMR (DMSO-d$_6$) 7.39–7.47 (m, 8H), 7.25 (d, 4H, J=9 Hz), 6.79 (d, 4H, J=9 Hz), 3.92 (s, 2H).

To synthesize a polycarbonate, bis[4-(4-hydroxyphenyl)phenyl]methane (0.34 g 0.96 mmol) was dissolved in 5 mL pyridine in a 25 mL one necked flask with stirring bar. Triphosgene (0.11 g, 0.35 mmol) was added to the pyridine solution, the flask capped immediately with a septum and stirred at room temperature. Ten hours later the reaction mixture was too thick for convenient stirring. The polymer was isolated by pouring the mixture into five times its volume of water with vigorous stirring. The polymer was filtered, washed with water, and suspended in 100 mL methanol at 80 degrees C. for 30 minutes with stirring. It was filtered and washed again, dried in a vacuum oven at 100 degrees C., providing 0.24 g product in 66% yield. NMR (CDCl3): 6.99 (4H, d), 7.36 (4H, d), 7.62 (4H, d), 7.73 (4H, d).

EXAMPLE 3

Synthesis of Polycarbonate of 2-(4-hydroxyphenyl)-2-[4-(4'-hydroxy-phenyl)phenyl]propane

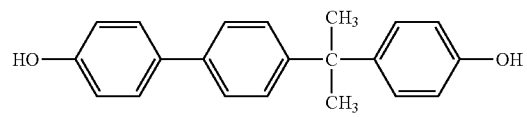

The following example sets forth an asymmetric bisphenol monomer and a resulting polymer of the present invention. The synthesis process also is generally shown by FIG. 3.

The process started with the synthesis of 2-(4-benzyloxylphenyl)-2-(4-hydroxyphenyl)propane. Bisphenol A (68.49 g, 300.0 mmol) was dissolved in a solution of sodium hydroxide (24.30 g, 607.5 mmol) in 1500 mL distilled water. Benzyl chloride (38.00 g, 300.2 mmol) was added to the resulting solution, heated to 75° C., over 30 min with vigorous stirring. Following 24 hour reflux, a solid precipitated upon cooling which was filtered, washed with water and dried in the hood. The crude product was recrystallized from toluene. The melting point was 107–108° C. The yield of product was 80.22 g (88.4%). $^1$H NMR (CDCl$_3$) 1.62 (6H, s, >C(—CH$_3$)$_2$), 5.02 (2H, s, PhCH$_2$O—), 6.72 (2H, d, aromatic protons ortho to the hydroxy group), 6.86 (2H, d, aromatic protons ortho to the benzyloxy group). 7.07–7.16 (4H, q, aromatic protons ortho to the isopropyl group), 7.31–7.44 (5H, m, aromatic protons of the benzyloxy group). IR (neat, cm$^{-1}$): 3300, 3192, 3034, 2817, 1601, 1581, 1511, 1466, 1453, 1381, 1362, 1301, 1249, 1233, 1183, 1102, 1084, 1015, 846, 828, 809, 769, 743, 697.

2-(4-benzyloxylphenyl)-2-(4-trifluoromethane-sulfonatephenyl)propane was synthesized as follows. A dry, three-necked, round-bottomed flask equipped with a magnetic stirring bar, argon gas inlet, and rubber septum was charged sequentially with monobenzylated BPA (22.82 g, 71.66 mmol) and 50 mL pyridine. The stirred solution was cooled to 0° C. and trifluoromethanesulfonic anhydride (13.5 mL, 80.2 mmol) was added via a syringe. The rate of addition was such that the internal temperature of the flask never exceeded 25° C. The solution was allowed to warm slowly to room temperature and maintained at room temperature for 25 hours. The reaction was quenched by pouring it into a 500 mL separatory funnel containing 100 mL of water and 150 mL of diethyl ether. The two phases were separated, and the aqueous phase extracted with four additional 80 mL portions of diethyl ether. The combined organic layer was washed twice with 100 mL 5% HCl aqueous solution, three times with ice-cold water, once with 100 mL brine, dried over anhydrous Na$_2$SO$_4$ and filtered. The solvent was removed on a rotary evaporator to yield a pale yellow solid. The yield was quantitative, 32 g. $^1$H-NMR (CDCl$_3$), $\delta_H$ 5.03 (2H, s, PhCH$_2$O—), 6.89 (2H, d, aromatic protons ortho to the benzyloxy group). 7.09–7.15 (4H, q, aromatic protons ortho to the isopropyl group), 7.27–7.44 (7H, m, other aromatic protons), IR (neat, cm$^{-1}$): 3300, 3192, 2817, 1601, 1581, 1510, 1233, 1015, 809, 769, 696.

The synthesis of 2-(4-benzyloxyphenyl)-2-[4-(4'-benzyloxyphenyl)phenyl]propane was as follows. A 250 mL one-necked round bottomed flask equipped stir bar was charged with a mixture of 2-(4-benzyloxylphenyl)-2-(4-trifluoromethanesulfonatephenyl)propane (4.50 g, 10.0 mmol), bis(4-benzyloxyphenyl)borinic acid (2.15 g, 5.45 mmol), and THF (80 mL) and potassium carbonate (1.92 g, 13.9 mmol in 100 mL water). The mixture was purged with argon for 2 minutes and Pd(PPh$_3$)$_4$ (0.090 g, 0.0778 mmol) was added under argon flushing. The flask was stirred under reflux and positive argon pressure for 12 hours. When the reaction finished, the THF was removed with a rotary evaporator. The slurry was extracted with 3×50 mL dichloromethane, the combined organic solution was filtered through a Buchner funnel with a silica gel pad, washed with another 50 mL dichloromethane, and the solvent of the filtrate was removed with a rotary evaporator, the residue was washed with 20 mL hexane, and the solid was filtered off and dried in a vacuum oven to afford 4.46 g (92%) product, $\delta_H$(CDCl$_3$) 5.03 (2H, s, PhCH$_2$—O— on the BPA phenyl ring), 5.10 (2H, s, PhCH$_2$O— on the biphenyl ring), 6.90 (2H, d, aromatic H of monophenyl ring ortho to benzyloxy group), 7.03 (2H, d, aromatic protons of biphenyl ring ortho to benzyloxy group), 7.18 (2H, d, the two aromatic protons ortho to the monophenyl ring), 7.28–7.52 (16H, m, and 10H from the benzyl aromatic protons, and 6H from protons of biphenyl group). IR (neat, cm$^{-1}$): 2872, 1607, 1509, 1452, 1363, 1259, 1220, 1180, 1152, 1085, 1044, 1022, 997, 815, 756, 735.

2-(4-hydroxyphenyl)-2-[4-(4'-hydroxyphenyl)phenyl]propane was synthesized as follows. To a 1000 mL round bottomed flask, 2-(4-benzyloxyphenyl)-2-[4-(4'-benzyloxyphenyl)phenyl]propane (3.0 g, 6.19 mmol) and 0.85 g 10% Pd/C were partially dissolved in 400 mL of ethyl acetate and debenzylated at atmospheric pressure and room temperature for 96 h. The catalyst was removed by filtration via a pad of Celite in a Buchner funnel, and the solvent was removed under reduced pressure at room temperature. The resulting solid was washed with 50 mL hexane and the solid was filtered off and dried. The yield was 1.88 g (quantitative). $^1$H NMR (solvent, CDCl$_3$): δ 1.68 (6H, >C(CH$_3$)$_2$), 6.75 (2H, d, ortho to the hydroxy group), 6.86 (2H, d, ortho to the hydroxy group), 7.13 (2H, d), 7.42–7.47 (4H, q). IR (neat, cm$^{-1}$): 3254, 2601, 2475, 2287, 2070, 1891, 1611, 1597, 1515, 1445, 1347, 1248, 1220, 1178, 1085, 1003, 848, 817, 783, 720.

To synthesize a polycarbonate, 2-(4-hydroxyphenyl)-2-[4-(4'-hydroxyphenyl)phenyl]propane (0.30 g, 0.99 mmol) was dissolved in 5 mL pyridine in a 25 mL one necked flask with stirring bar. Triphosgene (0.11 g, 0.37 mmol) was added. The flask was immediately capped with a septum and stirred at room temperature. After 10 minutes the reaction mixture had thickened. Stirring was continued overnight. The polymer was isolated by pouring the mixture into five times its volume of methanol with vigorous stirring. The polymer was filtered, washed with water, and suspended in 100 mL methanol at 80 degrees C. for 30 minutes with stirring. It was filtered and washed again, dried in a vacuum oven at 100 degrees C., providing 0.18 g product, 55%. Mw=11,217 with polydispersity of 2.10. Tg 177 degrees C. IR: 1773 (carbonyl). 1H-NMR (CDCl3): 7.15 (2H, m), 7.31 (4H, m), 7.47 (4H, m), 7.60 (2H, dd). Tg 177. Mw=57010; M$_N$=26070.

EXAMPLE 4

Polycarbonate of 1,1-bis[4-(4'-hydroxyphenyl)phenyl]-2,2-dichloroethene

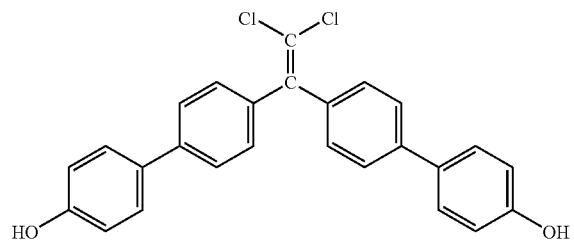

The following example sets forth the synthesis of another bisphenol monomer and a polymer containing a bisphenol monomer of the present invention. This monomer, the tetraaryl form of the DDT polycarbonate, was successfully synthesized by the Suzuki reaction using as the starting material the iodine analogue of DDT, a commercially available starting material.

The process started with the synthesis of 1,1'-(2,2,2-trichloroethylidene)bis[4-iodobenzene]. This procedure was an adaptation of that of Sumerford, W. T. *J. Am. Pharm. Assoc.* 1945, 34, 259. Chloral (8.40 g, 57.0 mmol) was mixed with iodobenzene (20.40 g, 100.0 mmol) in a round-bottomed flask affixed with reflux condenser and dropping funnel. The mixture was cooled in an ice/salt bath. Chlorosulfonic acid (7.0 mLs, 105 mmol) was added at the rate of approximately 1 mL every 10 minutes so as to maintain the temperature at no more than 5 degrees Celsius. The reaction mixture was allowed to warm to room temperature and maintained at room temperature for 2 hours. The dark purple mixture was poured over ice, upon which it solidified to give pink crystals. The solid was collected on a Buchner funnel, taken into ethyl acetate, and washed three times in a separatory funnel with water, once with dilute sodium bisulfite solution, again with water, and then with brine. After drying overnight over sodium sulfate, the organic solvent was removed to yield 15.78 g of product (29.36%) which after recrystallization from ethanol afforded white crystals of melting point 180° C. $^1$H NMR (300 MHz, CDCl$_3$ δ7.68 (d, J=8.5 Hz, 4H, Ar H), 7.31 (d, J=8.5 Hz, 4H, Ar H), 4.95 (s, 1H, CH).

1,1'-(2,2,2-trichloroethylidene)bis[4-(4'-methoxyphenyl) benzene] was then synthesized. The Suzuki reaction was performed after a literature method (Organic Syntheses, Volume 75, Amos B. Smith, III, editor, 1997, "Accelerated Suzuki Coupling via a Ligandless Palladium Catalyst: 4-Methyoxy-2'-methylbiphenyl (1,1'-biphenyl, 4'-methyoxy-2-methyl-) pages 61–68.) The iodo compound (20.00 g, 37.2 mmol) was mixed with 4-methoxyphenylboronic acid (12.45 g, 81.9 mmol) and refluxed for 24 hours with potassium carbonate (30.83 g, 223.0 mmol) and palladium acetate in 200 mL of acetone and water (50/50) under argon with stirring. The acetone was then removed by rotary evaporation and the remaining solution was taken into ethyl acetate and washed four times with water and once with brine. After drying overnight over sodium sulfate, the solvent was removed and the solid was recrystallized from ethanol. The recrystallized product was cream-colored with a yield of 84% (15.51 g, 33.6 mmol). $^1$H NMR (300 MHz, CDCl$_3$ δ 7.69 (d, J=8.5 Hz, 4H, Ar H), 7.50–7.55 (m, 4H, Ar H), 6.96 (d, J=8.5 Hz, 4H, Ar H), 5.13 (s, 1H, CH), 3.84 (s, 6H, CH$_3$).

1,1-bis[4-(4'-hydroxyphenyl)-phenyl]-2,2-dichloroethene was then synthesized. 1,1'-(2,2,2-trichloroethylidene)bis[4-(4'-methoxyphenyl)benzene] (5.00 g, 10.8 mmol) was added to a beaker and slowly heated to 110° C., at which time pyridinium hydrochloride (8.0 g, 69.2 mmol) was added to the beaker. The temperature was the slowly raised to 220° C. Three more 5 g portions of pyridinium hydrochloride were added over the course of the reaction. The temperature was held at 215–220° C. for 30 minutes. The resulting dark orange-brown liquid was poured with stirring into 600 mL of cold water. The solid was collected by filtration and recrystallized from aqueous ethanol (2%). The final product formed tan crystals, 4.49 g, 96% yield. $^1$H NMR (300 MHz, DMSO-d$_6$, δ): 9.59 (s, 2H, OH), 7.56 (d, J=8.6 Hz, 4H, Ar H), 7.48 (d, J=8.4, 4H, Ar H), 7.32 (d, J=8.7 Hz, 4H, Ar H), 6.81 (d, J=8.2 Hz, 4H, Ar H).

The synthesis of the polycarbonate of 1,1-bis[4-(4'-hydroxyphenyl)phenyl]-2,2-dichloroethene was as follows. Solution polycondensation polymerization of the chloral tetraaryl monomer was performed using triphosgene and pyridine as in previous methods. The product was only partially soluble in DMSO or CDCl$_3$. $^1$H NMR (300 MHz, DMSO-d$_6$, δ): 7.40–7.49 (m, 8H, Ar H), 7.72–7.49 (m, 8 H, Ar H). MW 68484.

EXAMPLE 5

Polycarbonate of bis[4-(4'-hydroxyphenyl)phenyloxy]methane

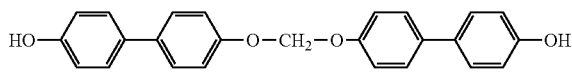

The following example sets forth another bisphenol monomer and a polymer containing a bisphenol monomer of the present invention.

The structurally-related aromatic polyformal obtained from bisphenol A and dichloromethane has a number of prominent physical properties comparable with those of Bisphenol A polycarbonate (BPA-PC). However, unlike BPA-PC, Bisphenol A polyformal (BPA-PF) additionally has excellent melt-flow and solvent resistant properties. Three synthetic routes, including phase transfer catalysis with two substrates and a Suzuki cross-coupling reaction were used to synthesize the desired monomer using commercially available 4,4'-Bisphenol or 4-bromophenol as starting material.

The process started with the synthesis of 4'-benzyloxybiphenyl-4-ol potassium salt. This compound was synthesized similar to the literature procedure for its preparation (Hay, A. S., Williams, H. M., Relles, Boulette, B. M., Donahue, P. B., Johnson, D. S. *J. Polym. Sci. Polym. Lett. Ed.* 1983, 21, 449; Hay, A. S., Williams, P. J., Relles, H. M., Boulette, B. M. *J. Macromol. Sci-Chem.* 1984, A21, 1065). A mixture of 4,4'-dihydroxybiphenyl (27.6 g, 100. mmol), 50% aqueous sodium hydroxide (8.00 g, 100. mmol in 16.0 mL water), 100 mL of DMSO and 100 mL of toluene was heated at reflux with a Dean Stark trap until all visible traces of water had been removed. The toluene was distilled from the system to give a homogeneous solution of 4'-benzyloxybiphenyl-4-ol in DMSO for the next reaction. The yield was considered quantitative. $^1$H NMR (DMSO-d6): δ 5.08 (2H, s, >CH$_2$), 6.70 (2H, d), 6.98 (2H, d), 7.29–7.44(9H. m). IR (neat, cm$^{-1}$): 3036, 2866, 2577, 2340, 1734, 1610, 1501, 1377, 1247, 1177, 1106, 1027, 1000, 815, 747, 700.

Bis[4-(4'-benzyloxyphenyl)phenyloxy]methane was synthesized by a Phenol Salt method (method 1), according to the literature procedure for its preparation (Hay, A. S., Williams, H. M., Relles, Boulette, B. M., Donahue, P. B., Johnson, D. S. *J. Polym. Sci. Polym. Lett. Ed.* 1983, 21, 449; Hay, A. S., Williams, P. J., Relles, H. M., Boulette, B. M. *J. Macromol. Sci-Chem.* 1984, A21, 1065). The above unisolated 4'-benzyloxybiphenyl-4-ol potassium salt solution was maintained at 110° C., and an excess of methylene chloride was added as rapidly as possible. The resulting mixture was heated at reflux for 2 hours. The distilled water was added, and the precipitated solid was isolated by filtration. The yield was quantitative. δ$_H$(CDCl$_3$) 5.11(4H, s, PhCH$_2$O—), 5.79(2H, s, —OCH$_2$O—),7.04(4H, d, biphenyl aromatic protons ortho to benzyloxy group), 7.18 (4H, d, biphenyl aromatic protons ortho to —OCH$_2$O— group), 7.33–7.51 (18H, m, 10H from PhCH$_2$O— aromatic protons, 8H from other biphenyl aromatic protons).

Bis[4-(4'-benzyloxylphenyl)phenyloxy)methane was also synthesized by a Phase transfer method (method 2). The phase transfer method used is that of Tanimoto, S. Imanishi, T., Jo, S., and Okano, M. "Syntheses of Formaldehyde Diaryl Acetals and Dithioacetals in the Presence of 18-Crown-6-Catalyst. Bull. Inst. Chem. Res., Kyoto Univ., Vol 56, 6, 297–299 (1978). To a 250 mL flask, 4'-benzyloxyphenyl-4-phenol (13.80 g, 50.00 mmol), sodium hydroxide (2.00 g, 50.0 mmol), 100 mL acetonitrile, and 12 mL water were added and stirred for 10 minutes at room temperature. The resulting solution was added dibromomethane 8.70 g (50.0 mmol) and 18-crown-6 ether (1.32 g, 5.00 mmol ). The reaction mixture was refluxing overnight, the white solid precipitated. The mixture was extracted with dichloromethane, washed with 70 mL distilled water three times, and combined organic phase, dried with sodium sulfate, removed the drying agent and solvent provided 24.25 g white solid (86%). The spectra data was identical with that of phenol salt method.

Bis[4-(4'-benzyloxyphenyl)phenyloxy]methane was also synthesized by a Phase Transfer/Suzuki Method (method 3). To a 250 mL flask 4-bromophenol (8.65 g, 50 mmol), sodium hydroxide (2.00 g, 50.0 mmol), 100 mL acetonitrile, and 12 mL water were added and stirred for 10 minutes at room temperature until dissolution. To the resulting solution were added dibromomethane (9.29 g, 50.0 mmol) and 18-crown-6 ether (1.32 g, 5.00 mmol). The reaction mixture was refluxing overnight, the white solid precipitated. The mixture was extracted with 2×100 mL dichloromethane, washed with 2×70 mL distilled water, 70 mL brine and combined organic phase, dried with sodium sulfate, removed the drying agent and solvent provided 7.87 g white solid of bis-(4-bromophenyloxy)methane (88%). $^1$H NMR (CDCl$_3$): $\delta_H$5.65 (2H, s, —OCH$_2$O—). 6.97(4H, d, aromatic protons ortho to the formal group), 7.39 (4H, d, aromatic protons ortho to bromine atom ). $^{13}$C NMR (CDCl$_3$), $\delta$91.16 (—OCH$_2$O—), 115.14, 118.30, 132.54, 155.88 (aromatic carbons). IR (neat, cm$^{-1}$): 1715, 1590, 1580, 1488, 1407, 1385, 1282, 1234, 1212, 1170, 1142, 1099, 1076, 1035, 1005, 821, 787, 665, 610, 600.

An oven-dried 100 mL one-necked round bottomed flask equipped with a stir bar was charged with a mixture of the preceding bis(4-bromophenyloxy)methane (0.72 g, 2.0 mmol ), bis(4-benzyloxyphenyl)borinic acid (1.72 g, 4.36 mmol) potassium fluoride (0.77 g, 13 mmol), and 30 mL dry THF. The mixture was purged with argon for 2 minutes, then Pd(OAc)$_2$ (0.022 g, 0.098 mmol) and P(Cy)$_3$ (0.03 g, 0.1 mmol) was added under argon flushing. The flask was capped with a rubber septum and stirred at room temperature for 48 hours. When finished, the THF was removed with a rotary evaporator. The residue was dissolved in 30 mL dichloromethane, filtered through a Buchner funnel with a silica gel pad, washed with another 20 mL dichloromethane, and the solvent of the filtrate was removed with a rotary evaporator, the residue was washed with 20 mL hexane, and the solid was filtered off and dried in a vacuum oven to afford 1.02 g (90%) product. The product the melting point, NMR spectra were identical to those of Method 1.

Bis[4-(4'-hydroxyphenyl)phenyloxy]methane was synthesized as follows. To a 1 L round-bottomed flask, bis(4'-benzyloxylbiphenyl-4-oxy)methane (5.64 g, 9.98 mmol) was partially dissolved in 100 mL of acetone and debenzylated at normal atmosphere pressure and at room temperature over 0.40 g palladium-on-charcoal (10% Pd) for 72 hours. Then the catalyst was removed by filtration and the solvent was removed under reduced pressure. The resulting gray residue was recrystallized from acetone, afforded 3.69 g product (96.2%). $^1$H NMR (DMSO-d$_6$): $\delta_H$ 5.84 (2H, s, —OCH$_2$O—), 6.79 (4H, d),7.10 (4H, d), 7.38 (4H, d), 7.49 (4H, D). $^{13}$C NMR (DMSO-d$_6$): $\delta$98.06 (—OCH$_2$O—), 116.17, 117.04, 127.65, 127.91, 130.99, 134.97, 155.64, 157.24 (aromatic carbons).

The bisphenol monomer was then polymerized in the following manner. Bis[4-(4'-hydroxyphenyl)phenyloxy]methane (0.34 g, 0.88. mmol) was dissolved in 5 ml pyridine in a 25 ml one-necked flask with stirring bar. Triphosgene (0.11 g, 0.37 mmol) was added to the pyridine solution and the flask was immediately capped with a septum and stirred at room temperature. After 10 minutes the reaction mixture had thickened and was allowed to stir overnight. The polymer was isolated by pouring the mixture into five times its volume of methanol with vigorous stirring. The polymer was filtered, washed with water, and suspended in 100 ml methanol at 80 degrees C. for 30 minutes with stirring. It was filtered and washed again, dried in a vacuum oven at 100 degrees C., providing 0.24 g product in 66% yield. 6.99 (4H, d), 7.36 (4H, d), 7.62 (4H, d), 7.73 (4H, d). $M_W$=1068; $M_N$=1049.

EXAMPLE 6

Polycarbonate of 1,1,1,3,3,3-hexafluoro-2-(4-hydroxyphenyl)-2-[4-(4'-hydroxyphenyl)phenyl]propane

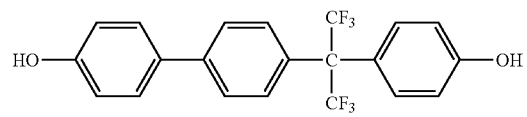

The following example sets forth another bisphenol monomer and a polymer containing a bisphenol monomer of the present invention.

The process started with the synthesis of 1,1,1,3,3,3-hexafluoro-2-(4-benzyloxyphenyl)-2-(4-hydroxyphenyl) propane. Hexafluorobisphenol A (23.53 g, 103.0 mmol) was dissolved in a solution of sodium hydroxide (8.24 g, 206.0 mmol) in 800 mL distilled water. The solution was heated to 75° C. and benzyl chloride (13.04 g, 103.0 mmol) was added over 30 min with vigorous stirring. Following 24 hour reflux, the mixture was cooled to room temperature, whereupon a white solid precipitated upon cooling which was filtered, washed with water three times and dried to give a white solid. $^1$H NMR (CDCl$_3$) 5.07 (2H, s, PhCH$_2$O—), 6.81(2H, d, aromatic protons ortho to the hydroxyl group), 6.95(2H, d, aromatic protons ortho to the benzyloxy group). 7.24–7.42 (9H, m, other aromatic protons). $^{13}$C NMR (CDCl$_3$): $\delta$ 70.12 (PhCH$_2$O—): 158.98 9 (aromatic carbons ortho to the benzyloxy group). 114.33, 1115.04, 127.62, 128.23, 128.72, 131.73, 136.56, 156.10, 158.98 (other aromatic carbons). IR (neat, cm$^{-1}$): 3435, 1609, 1578, 1500, 1376, 1263, 1233, 1176, 1042, 995, 814, 791.

1,1,1,3,3,3-hexafluoro-2-(4-benzyloxylphenyl)-2-(4-trifluoromethanesulfonatephenyl)propane was then synthesized. A dry, three-necked, round-bottomed flask equipped with a magnetic stirring bar, argon gas inlet, and rubber septum was charged with 1,1,1,3,3,3-hexafluoro-2-(4-benzyloxylphenyl)-2-(4-hydroxyphenyl)propane (10.66 g, 25.00 mmol) and 30 mL pyridine. The stirred solution was cooled to 0° C. and trifluoromethanesulfonic anhydride (7.86 g, 27.9 mmol) of was added through septum via syringe. The rate of addition was such that the internal temperature of the flask remained under 25° C. The solution was allowed to warm slowly to room temperature and maintained at room temperature for 25 hr. The reaction mixture was poured into a 500 mL separatory funnel containing 100 mL of water and 150 mL of diethyl ether. The two phases were separated and the aqueous phase was extracted with four additional 50 mL portions of diethyl ether. The combined organic layer was washed twice with 50 mL 5% HCl aqueous solution, then three times with ice-water, then 50 mL brine, and the organic phase was dried over anhydrous Na$_2$SO$_4$. The solvent was removed on a rotary evaporator to afford a pale yellow, wax-like solid. The yield was quantitative. $^1$H NMR (CDCl$_3$): $\delta_H$ 5.07 (2H, s, PhCH$_2$O—), 6.96 (2H, d, aromatic protons ortho to the benzyloxy group). 7.27–7.53 (11H, m, other aromatic protons). $^{13}$C NMR(CDCl$_3$): δ 68.03 (—C(CF$_3$)$_2$), 70.16 (PhCH$_2$O—), 114.33 and 114.69 (—C(CF$_3$)$_2$, 149.66 (aromatic carbons ortho to the benzyloxy group 159.31(—OSO$_2$CF$_3$). 121.14, 121.61, 124.65, 127.60128.28, 128.75, 131.40, 132.29, 132.43, 134.23, 136.40.

1,1,1,3,3,3-hexafluoro-2-(4-benzyloxyphenyl)-2-[4-(4'-benzyloxyphenyl)phenyl]propane was then synthesized as follows. A 250 mL one-necked round bottomed flask equipped with a stir bar was charged with a mixture of 1,1,1,3,3,3-hexafluoro-2-(4-benzyloxylphenyl)-2-(4-trifluoromethanesulfonatephenyl)propane (5.58 g, 10.0 mmol), bis(4-benzyloxyphenyl)borinic acid (2.15 g, 5.45 mmol), 80 mL THF and potassium carbonate (1.92 g, 13.9 mmol in 100 mL water). The resulting mixture was purged with argon for 2 minutes, then Pd(PPh$_3$)$_4$ (0.090 g, 0.078 mmol) was added with argon flushing. The flask was stirred under reflux and positive argon pressure for 12 hours. Reaction progress was monitored by TLC and NMR analysis. When the reaction finished, the THF was removed by rotary evaporation. The slurry was extracted with 3×50 mL dichloromethane, and the combined organic solutions were filtered through a Buchner funnel with a silica gel pad The silica gel was washed with another 50 mL dichloromethane. Solvent was removed by rotary evaporation, the residue was washed with 20 mL hexane, and the solid was collected by filtration and dried in a vacuum oven to afford 5.69 g (96%) product, H NMR (CDCl$_3$): δ 5.08 (2H, s, PhCH$_2$O—), 5.11(2H, s, another PhCH$_2$O—), 6.97 (2H, d, aromatic protons of monophenyl ring ortho to the benzyloxy group), 7.06 (2H, d, aromatic protons of the biphenyl rings ortho to the benzyloxy group), 7.18 (2H, d, other two aromatic protons of monophenyl ring rings ortho to the benzyloxy group) 7.06–7.54 (16H, m, 10H from the two benzyl group's aromatic protons, and 6H from other protons of biphenyl group). IR (neat, cm$^{-1}$): 11608, 1570, 1500, 1454, 1378, 1283, 1237, 1177, 1033, 991, 917, 813, 794, 745, 698.

1,1,1,3,3,3-hexafluoro-2-(4-hydroxyphenyl)-2-[4-(4'-hydroxyphenyl)phenyl]propane was synthesized as follows. The previous 1,1,1,3,3,3-hexafluoro-2-(4-benzyloxyphenyl)-2-[4-(4'-benzyloxyphenyl)phenyl]propane, (4.74 g, 80.0 mmol) and 0.5 g 10% Pd/C were dissolved in 200 mL of ethyl acetate and debenzylated at normal atmosphere pressure and at room temperature for 96 hours. Then the catalyst was removed by filtration via a pad of Celite in a Buchner funnel, and the solvent was removed under reduced pressure and at room temperature. The resulting straw-colored oil was dried in vacuum. The yield was 3.30 g (quantitative). $^1$H NMR (CDCl$_3$): δ$_H$ 6.85 (2H, d, ortho to the hydroxyl group), 6.93 (2H, d, ortho to the hydroxyl group), 7.28 (2H, d), 7.42–7.57 (4H, q). IR (neat, cm$^{-1}$): 3485, 1773, 1609, 1576, 1496, 1303, 1163, 1108, 1031, 997, 817.

A polycarbonate of 1,1,1,3,3,3-hexafluoro-2-(4-hydroxyphenyl)-2-[4'-(4-hydroxyphenyl)phenyl]propane was synthesized as follows. A solution of 1,1,3,3,3-hexafluoro-2-(4-hydroxyphenyl)-2-[4-(4'-hydroxyphenyl)phenyl]propane (0.30 g, 0.73 mmol) and 1N aqueous sodium hydroxide (3 mL) was prepared and cooled to 0–5° C. Triphosgene (0.09 g, 0.31 mmol) and benzyltriethylammonium chloride (10 mg) were added to the sodium hydroxide solution which was immediately capped. The two phases were stirred at 0–5° C. for 15 minutes and at 10–15° C. for 45 minutes. The organic phase was separated and poured into methanol (200 mL) and the precipitated polymer was filtered. After repeated precipitation in methanol, the polymer was obtained in 66% yield. $^1$H NMR (300 MHz, CDCl$_3$): δ 7.58–7.64 (m, 4H, ArH), 7.47–7.52 (m, 4H, ArH), 7.36–7.41 (m, 4H, ArH). $M_w$=20010, $M_n$=10330, PDI=1.9.

EXAMPLE 7

2,2-bis[4-(3'-hydroxyphenyl)phenyl]propane

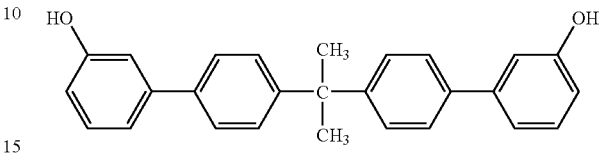

The following example sets forth another bisphenol monomer and a polymer containing a bisphenol monomer of the present invention.

The process started with the synthesis of 2,2-bis[4-(3'-methoxyphenyl)phenyl]propane. A solution of 2,2-bis(4-iodophenyl)propane (0.90 g, 2.01 mmol) and 3-methoxyphenylboronic acid (0.67 g, 4.41 mmol) in acetone (3 mL) was made. A second solution of potassium carbonate (1.66 g, 12.0 mmol) in water (3 mL) was added, and the reaction mixture was stirred 5 minutes to gentle reflux. After evacuation and flushing with argon, palladium(II)acetate (5 mg) was added. The suspension was heated for 3 hours at reflux and positive argon pressure. Upon cooling to room temperature, the crude product was extracted with methylene chloride (4×30 mL) and washed with water (2×30 mL) and brine (1×30 mL). The combined organic layers were dried (Na$_2$SO$_4$) and concentrated under reduced pressure. The residue was recrystallized from ethanol to afford the title compound (0.55 g, 67%) as tan crystals. $^1$H NMR (300 MHz, CDCl$_3$): δ 7.50–7.53 (d, J=8.4 Hz, 4H, ArH), 7.31–7.36 (m, 6H, ArH), 7.16–7.18 (d, J=7.7 Hz, 2H, ArH), 7.12 (s, 2H, ArH), 6.86–6.89 (d, J=8.2 Hz, 2H, ArH), 3.85 (s, 3H, OCH$_3$), 1.75 (s, 6H, CH$_3$).

2,2-bis[4-(3'-hydroxyphenyl)phenyl]propane was synthesized as follows. The previous 2,2-bis[4-(3'-methoxyphenyl)phenyl]propane (1.00 g, 2.45 mmol) and pyridine hydrochloride (5.20 g, 45.0 mmol) were added to a beaker and slowly heated to 210–230° C. with stirring. Two more 4 g portions of pyridine hydrochloride were added over the course of the reaction. The temperature was held at 210–230° C. for 1 hour. The resultant viscous, dark, red-brown liquid was poured while being stirred into 200 mL of water. The solid was collected by filtration. The final product (0.86 g, 92%) was isolated as fine crystals. $^1$H NMR (300 MHz, DMSO-d$_6$): δ 9.49 (br.s. 2H, exchangeable with D$_2$O, OH), 7.47–7.49 (d, 4H, ArH), 7.27–7.30 (d, 2H, ArH), 7.17–7.22 (t, 4H, ArH), 6.99–7.02 (d, 2H, ArH), 6.95 (s, 2H, ArH), 6.68–6.72 (d, 2H, ArH), 1.66 (s, 6H, CH$_3$).

A polycarbonate of 2,2-bis[4-(3'-hydroxyphenyl)phenyl] propane was synthesized as follows. A solution of 2,2-bis [4-(3 '-hydroxyphenyl)phenyl]propane (0.19 g, 0.50 mmol) and 1N aqueous sodium hydroxide (2 mL) was prepared and cooled to 0–5° C. Triphosgene (0.06 g, 0.21 mmol) and benzyltriethylammonium chloride (5 mg) were added to aqueous 1N sodium hydroxide solution immediately. Then both phases were rapidly stirred at 0–5° C. for 15 minutes and at 10–15° C. for 45 minutes. The organic phase was separated and poured into methanol (200 mL) and the precipitated polymer was filtered.

EXAMPLE 8

Tetraarylbisphenol A dimethacrylate

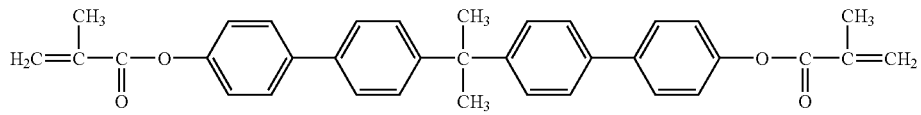

This is an example showing the synthesis of a derivative of tetraaryl Bisphenol A and has particular potential for advantageous use in resin markets. Tetraaryl BPA, 3.80 g (0.010 moles), was dissolved in 200 mL of dichloromethane in a 500 mL round-bottomed flask. Triethylamine, 2.53 g (0.025 moles), was added with stirring under argon in an ice to give a clear, dark brown solution. A solution methacryloyl chloride, 2.61 g (0.025 moles), in 15 mL of dichloromethane was added dropwise with constant stirring. After 1.5 hours stirring the solution was washed three times with water, once with brine, and organic layer was dried over sodium sulfate. The dichloromethane was removed by rotary evaporation to give a tan solid which was then dried in a dessicator to give 5.02 g (97% yield) of pure product, mp 170–171° C. H-NMR(CDCl$_3$) d1.76 (s, 6H), 2.08 (s, 6H), 5.77 (s, 2H), 6.37 (s, 2H), 7.18 (d, J=806 Hz, 4H), 7.34 (d, J=8.5 Hz, 4H), 7.50 (d, J=8.4 Hz, 4H), 7.60 (d, J=8.7 Hz, 4H).

EXAMPLE 9

Tetraarylbisphenol A diglycidyl ether

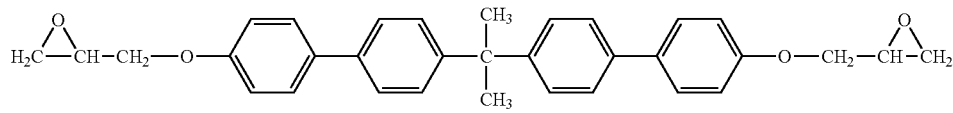

This is another example showing the synthesis of a derivative of tetraaryl Bisphenol A and has particular potential for advantageous use in resin markets. Sodium hydroxide, 0.10 g (2.05 mmol) was dissolved in 20 mL of water in a two-necked, 100 mL round-bottomed flask. Tetraaryl BPA, 0.38 g (1.00 mmol), was added to form a cloudy brown solution which was heated to 50° C. under constant stirring. The solution was cooled to 30° C. and epichlorohydrin, 0.22 g (2.35 mmol), was added dropwise. The solution was heated to 60–65° C. for one hour after which time solution became viscous. Water (10 mL) was added to dilute the thick solution. The solution was heated to 70–75° C. for 27 hours. Subsequently, the reaction solution was cooled and extracted with toluene and washed three times with water. The toluene was evaporated at atmospheric pressure overnight to give a white solid. The solid was washed in hot ethanol to remove excess tetraaryl BPA, and 0.21 g (43% yield) of the white solid was collected by suction filtration, mp 252–253° C. H-NMR(DMSO-d$_6$) d1.76 (s, 6H), 3.33 (d), 4.0–4.2 (m), 5.44 (d), 6.99 (d), 7.25 (d), 7.47–7.53(m).

EXAMPLE 10

Tetraarylbisphenol A Dicyanate

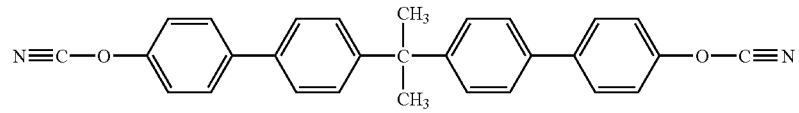

This is yet another example showing the synthesis of a derivative of tetraaryl Bisphenol A and has particular potential for advantageous use in resin markets. Tetraaryl BPA, 0.38 g (1.0 mmol), and 0.22 g (2.1 mmol) cyanogen bromide were dissolved in approximately 10 ml of dry acetone in a 25 mL round-bottomed flask The contents were cooled in an ice bath and triethylamine, 0.29 mL (2.1 mmol), was added dropwise over 30 minutes with constant stirring. The reaction solution was allowed to stir an additional 60 minutes at room temperature. The solution was extracted with dichloromethane, washed twice with water, once with brine and dried over sodium sulfate. The solvent was removed by rotary evaporation affording 0.32 g (74% of theoretical) of dark brown crystals. Mp: 132–133° C. $^1$NMR(DMSO-d$_6$) d7.78 (d, 4H, J=9 Hz), 7.57 (d, 4H, J=9 Hz), 7.48 (d, 4H, J=9 Hz), 7.32 (d, 4H, J=9 Hz), 1.66 (s, 6H).

EXAMPLE 11

1,1-Dichloro-2,2-bis[4-(4'-Hydroxyphenyl)Phenyl] Ethene and Homo- and Heteropolymers Polycarbonates from 1,1-dichloro-2,2-bis-(4-hydroxyphenyl)ethylene (BPC) are a highly flame-resistant family of engineering thermoplastics. This example shows the synthesis of a monomer of the present invention, 1,1-dichloro-2,2-bis[4'-(4-hydroxyphenyl)phenyl]ethane (TA- BPC). Polymerization was by solution polycondensation of TA-BPC with different dihydroxydiaryl compounds using triphosgene The process started with the synthesis of 2,2-bis(4-iodophenyl)-1,1,1-trichloroethane, I-DDT. Chloral (16.2 g, 0.11 mol), was mixed with iodobenzene (40.8 g, 0.20 mol), and the mixture was stirred and cooled to 5 °C. Chlorosulfonic acid (12 mL, 0.18 mol) was then added at a rate of mL every 10 minutes and the temperature was maintained at 5° C. The reaction mixture was allowed to warm and after reaching room temperature, then stirred for 2 hours. The dark purple mixture was poured over ice, whereupon it formed pink crystals. The crystals were filtered and washed with water (3×150 mL), then taken into ethyl acetate, washed with dilute sodium bisulfite solution (150 mL) and then with brine (150 mL). The organic layer was dried ($Na_2SO_4$) and concentrated. The residue was recrystallized from ethanol to afford the title compound I-DDT (26.9 g, 50%) as white needles, mp 179–180° C. $^1$H NMR (300 MHz, $CDCl_3$) δ 7.65–7.70 (d, J=8.5 Hz, 4H, ArH), 7.28–7.33 (d, J=8.5 Hz, 4H, ArH), 4.95 (s, 1H, C$\underline{H}$).

1,1-dichloro-2,2-bis[4-(4'-methoxyphenyl)-phenyl]ethane was then synthesized as follows. I-DDT (29.5 g, 0.055 mol) and 4-methoxyphenylboronic acid (18.4 g, 0.121 mol) were dissolved in acetone (100 mL). A solution of potassium carbonate (45.6 g, 0.33 mol) in water (100 mL) was then added and reaction mixture was stirred 5 minutes to gentle reflux. After evacuation and flushing with argon, palladium(II)acetate (10 mg, 0.04 mmol) was added and the suspension was heated for 10 hours under reflux and positive argon pressure. It was then cooled to room temperature and extracted with ethyl acetate (4×200 mL), washed with water (2×100 mL) and brine (1×150 mL). The combined organic layers were dried ($Na_2SO_4$) and concentrated under reduced pressure. The residue was recrystallized from ethanol to afford the title compound (25.7 g, 94%) as white crystals. $^1$H NMR (300 MHz, $CDCl_3$) δ 7.68–7.70 (d, J=8.0 Hz, 4H, ArH), 7.50–7.53 (m, 8H, ArH), 6.95–6.98 (d, J=8.1 Hz, 4H, ArH), 3.84 (s, 3H, OC$\underline{H}_3$).

1,1-dichloro-2,2-bis[4-(4'-hydroxyphenyl)phenyl]ethene, (TA-BPC) was then synthesized. 1,1-dichloro-2,2-bis[4-(4'-methoxyphenyl)phenyl]ethene (10.00 g, 0.020 mol) and pyridine hydrochloride (16.73 g, 0.138 mol) were added to a beaker and slowly heated with stirring to 215–220° C. Three additional 10 g portions of pyridine hydrochloride were added over the course of the reaction. The temperature was held at 215–220° C. for 30 minutes. The viscous, dark reddish-brown liquid obtained was poured with stirring into 500 mL of water. The solid was collected by filtration and recrystallized from ethanol/water. The final product TA-BPC (8.34 g, 96%) was fine light yellow crystals. IR (KBr) 3520, 3300–2600, 3034, 1609, 1595, 1527, 1497, 1252, 1171, 1110, 960, 861, 823, 509 cm$^{-1}$. $^1$H NMR (300 MHz, DMSO-$d_6$) δ 9.59 (br.s. 2H, exchangeable with $D_2O$, O$\underline{H}$), 7.56–7.59 (d, J=8.6 Hz, 4H, ArH), 7.45–7.49 (d, J=8.4 Hz, 4H, ArH), 7.30–7.34 (d, J=8.7 Hz, 4H, ArH), 6.80–6.82 (d, J=8.2 Hz, 4H, ArH).

Homopolycarbonate (PC TA-BPC) was synthesized in accordance with a known method. See Sun, S. J.; Hsu, K. Y.; Chang, T. C. Polym. J. 1997, 29, 25. TA-BPC (0.217 g, 0.5 mmol) was dissolved in 5.8 mL of pyridine and the solution was cooled to 0° C. A solution of triphosgene (0.062 g, 0.21 mmol) in methylene chloride (2 mL) was added dropwise and the reaction mixture was vigorously stirred at 0–5° C. for 15 minutes. The solution became viscous and saturated with pyridine-hydrochloride after this time and was subsequently warmed to room temperature. The suspension was then stirred for an additional 4 hours. A 5% aqueous hydrochloric acid (10 mL) was used to neutralize the reaction mixture. The polymer was extracted with methylene chloride (3×2 mL), washed with water (3×2 mL), and the combined organic layers were dried ($MgSO_4$) and concentrated. The viscous residue was poured into methanol. The precipitated polymer was filtered, washed with methanol and dried at 40° C. under vacuum for 24 hours (0.20 g, 88% yield). IR (KBr) 3032, 1771, 1610, 1590, 1494, 1225, 1185, 1161, 1005, 974, 860, 821, 514 cm$^{-1}$. $^1$H NMR (300 MHz, $CDCl_3$) δ 7.35–7.41 (m, 8H, ArH), 7.55–7.58 (d, J=7 Hz, 4H, ArH), 7.62–7.65 (m, J=7.6 Hz, 4H, ArH).

A variety of copolycarbonates were synthesized. Bisphenol A (BPA), Bisphenol C (BPC), 4,4'-(hexafluoroisopropylidene)diphenol (HFBPA) and 4,4'-sulfonyl diphenol (SBPA) were used as co-monomers. All copolymers (PC TABPC-BPA, PC TABPC-BPC, PC TABPC-HFBPA and PC TABPC-SBPA) were prepared using triphosgene similar to the above method for the synthesis of the homopolymer. The copolycarbonates were characterized by IR, $^1$H NMR and HPLC-GPC.

The synthesis of desired 1,1-dichloro-2,2-bis[4-(4'-hydroxyphenyl)phenyl]ethane (TA-BPC) proceeded in three steps starting from iodobenzene The synthesis of I-DDT took advantage of previously described procedures, See Sumerford, W. T.; J. Am. Pharm. Assoc. 1945, 34, 259. Three DDT-like synthesis were initially attempted in order to synthesize the I-DDT analogue. The first used 0.1 mol of iodobenzene and 0.4 mol of sulfuric acid. This synthesis gave the desired product, albeit in low yield (20–30%). Fuming sulfuric acid as condensing agent resulted in sulfonation of the iodobenzene rather than the desired product. Best results were achieved with chlorosulfonic acid as condensing agent, giving the desired product in 50% yield. The Suzuki cross-coupling reaction was used to add the two additional aryl rings in the second step of synthesis. Our earlier research indicated that the Suzuki reaction using 4-methoxyphenylboronic acid yielded excellent results when performed on the iodine analogue of BPA. Thus, aryl coupling of I-DDT was carried out under reflux and a positive argon pressure using 2.2 equiv of 4-methoxyphenylboronic acid precursor, 6 equiv of potassium carbonate as mildly base and palladium(II)acetate as ligandless catalyst precursor in acetone-water. 1,1-Dichloro-2,2-bis[4'-(4-methoxyphenyl)phenyl]ethene was obtained in high yield (94%). Several deprotection reagents and protocols for the methoxy group were tried, with best results obtained using pyridine hydrochloride. For the latter, 1,1-dichloro-2,2-bis [4'-(4-methoxyphenyl)phenyl]ethene was subjected to fusion with pyridine hydrochloride, resulting in di-demethylation and simultaneous dehydrochlorination to provide the final product TA-BPC in excellent yield (96%).

The polycarbonates were synthesized from TA-BPC and various aromatic diols with triphosgene by solution polycondensation method in pyridine and methylene chloride. Pyridine serves as both excellent solvent and hydrogen chloride scavenger. Triphosgene was chosen as a phosgene substitute for practical reasons, although phosgene is also used to increase the molecular weights in subsequent polymerizations. Being a solid, triphosgene is safer and easier-to-handle and accurate amounts can be weighed, limiting side reactions due to excess reagent.

The polycondensation was examined using various amounts of triphosgene in order to find the optimal reaction conditions, and amounts varied from 0.3 to 0.6. The results are summarized in FIG. 4. The molecular weight and yield of the polymers show a marked dependence on the amount of triphosgene. Polycondensation with 0.42 mmol of triphosgene to 1 mmol of diols gave the best results. The polymers were isolated as white powdery materials by extraction into methylene chloride, water washing, and precipitation into methanol. In this manner the by-product pyridine hydrochloride dissolved in water and the chloroformate-pyridine complex at both ends of the polymer chain was decomposed.

A series of three TABPC-BPC copolycarbonates was prepared and the molar ratio of TA-BPC and BPC was varied from 25/75 to 75/25 in steps of 25 mol %. The yields and characteristics of the resulting polymers are shown in FIG. 4. All polymers were soluble in chlorinated solvents and THF. These polymers have good solubility.

All synthesized copolycarbonates were soluble in chlorinated solvents and films were able to be cast from solvent. Only the homopolymer of TA-BPC evidenced poorer solubility in all common organic solvents, necessitating its workup with considerably more methylene chloride for dissolution than the other copolymers. The IR spectra of the isolated polycarbonates exhibited the characteristic bands for the aromatic polycarbonate system, including a strong absorption band at 1774 $cm^{-1}$, assigned to the stretching vibration of C=O group, phenyl group at 1610, 1593, 1496 $cm^{-1}$, ether group at 1228, 1186, 1162 $cm^{-1}$ and deformation vibration at 823 $cm^{-1}$ assigned to the 1,4-disubstitution of the aromatic rings. The IR spectra showed two bands at about 86 and 514 $cm^{-1}$, due to the skeletal vibration of the C—Cl bond, and at 974 $cm^{-1}$ indicative of the out-of-plane deformation vibration of >C=C<. The $^1$H NMR spectra demonstrated the successful incorporation of both aromatic diols into the polymer chain. The $^1$H NMR spectra of TABPC-BPC copolycarbonates for each of molar ratio 25/75, 50/50 and 75/25 indicates equimolar incorporation of the diols and demonstrated the successful incorporation of monomers into the final copolymers. The combinations of TA-BPC monomer with BPC, HFBPA and SBPA diols resulted in polymers having a coefficient of polydispersity ranging from 1.3 to 1.6.

An efficient synthesis of the new monomer 1,1-dichloro-2,2-bis[4-(4'-hydroxyphenyl)phenyl]ethene, TA-BPC, has been achieved in three steps with high purity and overall yield of 45–50% nearly 40 years after its diaryl analogue. The structure has been confirmed by IR and $^1$H NMR. Using the pure tetraaryl and diarylaromatic diols Bisphenol A, Bisphenol C, Hexafluorobisphenol, and Sulfonylbisphenol, solution polycondensation of these monomers with triphosgene was successful. All copolycarbonates were soluble in chlorinated solvents and films could be cast from solvent. Only the homopolymer of TA-BPC was of lowered solubility in all common organic solvents tried. Good incorporation of the monomer into the polymer has been demonstrated.

The foregoing discussion of the invention has been presented for purposes of illustration and description. The foregoing is not intended to limit the invention to the form or forms disclosed herein. In the foregoing Detailed Description for example, various features of the invention are grouped together in one or more embodiments for the purpose of streamlining the disclosure. This method of disclosure is not to be interpreted as reflecting an intention that the claimed invention requires more features than are expressly recited in each claim. Rather, as the following claims reflect, inventive aspects lie in less than all features of a single foregoing disclosed embodiment. Thus, the following claims are hereby incorporated into this Detailed Description, with each claim standing on its own as a separate preferred embodiment of the invention.

Moreover though the description of the invention has included description of one or more embodiments and certain variations and modifications, other variations and modifications are within the scope of the invention, e.g. as may be within the skill and knowledge of those in the art, after understanding the present disclosure. It is intended to obtain rights which include alternative embodiments to the extent permitted, including alternate, interchangeable and/or equivalent structures, functions, ranges or steps to those claimed, whether or not such alternate, interchangeable and/or equivalent structures, functions, ranges or steps are disclosed herein, and without intending to publicly dedicate any patentable subject matter.

What is claimed is:

1. A bisphenol of a formula:

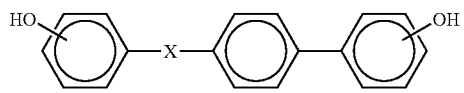

wherein X is a spacer group selcted from the group consisting of

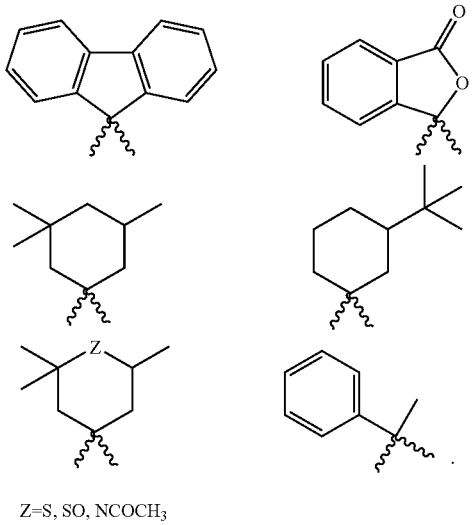

Z=S, SO, NCOCH$_3$

2. A bisphenol of a formula:

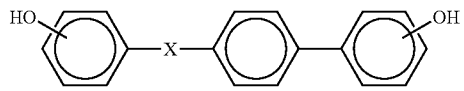

wherein X is a spacer group selected from the group consisting of substituted alkyl radicals, unsubstituted alkyl radicals, substituted benzyl radicals, unsubstituted benzyl radicals, carbonyl radicals, sulfides, sulfones, sulfoxides, and mixtures of combinations thereof, and wherein at least one of the aryl units is substituted.

3. A bisphenol of a formula:

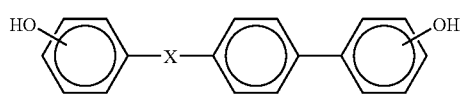

wherein X is a spacer group selected from the group consisting of substituted alkyl radicals, unsubstituted alkyl radicals, substituted benzyl radicals, unsubstituted benzyl radicals, carbonyl radicals, sulfides, sulfones, sulfoxides, and mixtures of combinations thereof, and wherein the hydroxyl end groups are bonded to a terminal aryl group at a position selected from the group consisting of a meta position and an ortho position.

4. The bisphenol of claim 1, wherein the spacer group is selected from the group consisting of $CH_2$, $C(CF_3)_2$, $O-CH_2-O$, and $C(CH_3)_2$.

5. A polymer comprising at least one monomer unit of the bisphenol of claim 1.

6. A resin comprising at least one derivative of the bisphenol of claim 1.

7. A derivative of the biophenol of claim 1.

8. A composition comprising a formula:

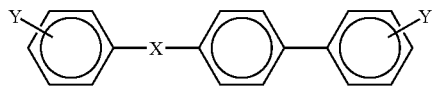

wherein X is a spacer group selected from the group consisting of substituted alkyl radicals, unsubstituted alkyl radicals, substituted benzyl radicals, unsubstituted benzyl radicals, carbonyl radicals, sulfides, sulfones, sulfoxides, and mixtures of combinations thereof; and Y is an end group other than a hydroxyl radical or an ether.

9. A composition having a formula:

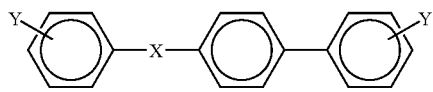

wherein X is a spacer group selected from the group consisting of substituted alkyl radicals, unsubstituted alkyl radicals, substituted benzyl radicals, unsubstituted benzyl radicals, carbonyl radicals, sulfides, sulfones, sulfoxides, and mixtures of combinations thereof; and Y is an end group is selected from the group consisting of methyl acrylates, glycidyl ethers and cyanates.

10. A composition having a formula:

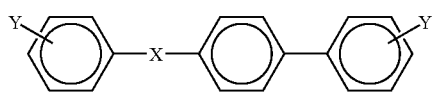

wherein Y is an end group other than a hydroxyl radical and X is a spacer group selected from the group consisting of

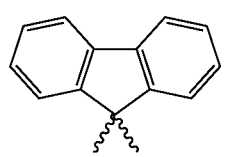 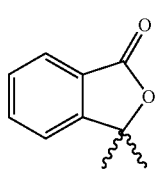

-continued

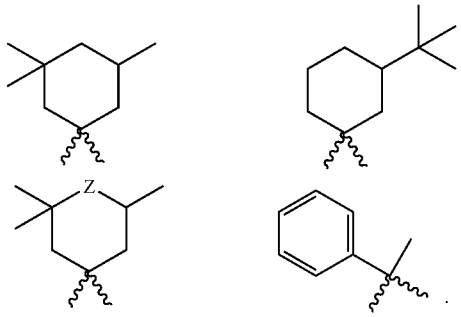

Z=S, SO, NCOCH₃

11. The composition of claim 10, wherein the end group is selected from the group consisting of methyl acrylates, glycidyl ethers, and cyanates.

12. A composition having a formula:

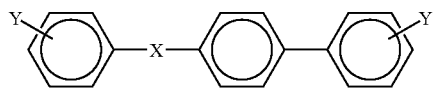

wherein X is a spacer group selected from the group consisting of substituted alkyl radicals, unsubstituted alkyl radicals, substituted benzyl radicals, unsubstituted benzyl radicals, carbonyl radicals, sulfides, sulfones, sulfoxides, and mixtures of combinations thereof; Y is an end group other than a hydroxyl radical; and wherein at least one of the aryl units is substituted.

13. A composition having a formula:

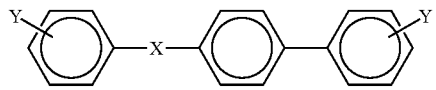

wherein X is a spacer group selected from the group consisting of substituted alkyl radicals, unsubstituted alkyl radicals, substituted benzyl radicals, unsubstituted benzyl radicals, carbonyl radicals, sulfides, sulfones, sulfoxides, and mixtures of combinations thereof; Y is an end group other than a hydroxyl radical; and wherein the end groups are bonded to a terminal aryl group at a position selected from the group consisting of a meta position and an ortho position.

14. A polymer comprising at least one monomer unit of the composition of claim 9.

15. A resin comprising at least one derivative of a composition having a formula:

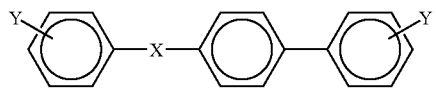

wherein X is a spacer group selected from the group consisting of substituted alkyl radicals, unsubstituted alkyl radicals, substituted benzyl radicals, unsubstituted benzyl radicals, carbonyl radicals, sulfides, sulfones, sulfoxides, and mixtures of combinations thereof; and Y is an end group other than a hydroxyl radical.

16. The bisphenol of claim 2, wherein the spacer group is selected from the group consisting of $CH_2$, $C(CF_3)_2$, $O—CH_2—O$, and $C(CH_3)_2$.

17. A polymer comprising at least one monomer unit of the bisphenol of claim 2.

18. A resin comprising at least one derivative of the bisphenol of claim 2.

19. A derivative of the biophenol of claim 2.

20. The bisphenol of claim 3, wherein the spacer group is selected from the group consisting of $CH_2$, $C(CF_3)_2$, $O—CH_2—O$, and $C(CH_2)_2$.

21. A polymer comprising at least one monomer unit of the bisphenol of claim 3.

22. A resin comprising at least one derivative of the bisphenol of claim 3.

23. A derivative of the biophenol of claim 3.

24. A polymer comprising at least one monomer unit of the composition of claim 10.

25. A polymer comprising at least one monomer unit of the composition of claim 11.

26. A polymer comprising at least one monomer unit of the composition of claim 12.

27. A polymer comprising at least one monomer unit of the composition of claim 13.

28. A composition having a formula:

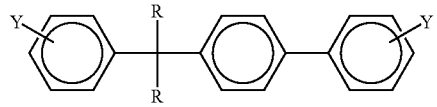

wherein R is a $C_{1-4}$ primary alkyl or a $C_{6-10}$ cycloalkyl and is Y is an end group.

29. The composition of claim 28, wherein the end group is selected from the group consisting of hydroxyl, ethers, methyl acrylates, glycidyl ethers, and cyanates.

* * * * *

UNITED STATES PATENT AND TRADEMARK OFFICE
CERTIFICATE OF CORRECTION

| | | |
|---|---|---|
| PATENT NO. | : 7,125,951 B2 | Page 1 of 1 |
| APPLICATION NO. | : 10/692970 | |
| DATED | : October 24, 2006 | |
| INVENTOR(S) | : David A. Boyles et al. | |

It is certified that error appears in the above-identified patent and that said Letters Patent is hereby corrected as shown below:

Column 1, line 15, before the section entitled "FIELD OF INVENTION", insert the following new section:

--GOVERNMENT FUNDING

The invention described herein was made with government support under the Army Research Office Grant No. W911NF-05-1-0424 CFDA#12.431. The United States Government has certain rights to this invention.--

Signed and Sealed this
Eleventh Day of January, 2011

David J. Kappos
*Director of the United States Patent and Trademark Office*